US012396913B2

(12) United States Patent
Romo

(10) Patent No.: US 12,396,913 B2
(45) Date of Patent: Aug. 26, 2025

(54) INTERFACE FOR AN EXOSKELETON

(71) Applicant: OSSUR ICELAND EHF, Reykjavik (IS)

(72) Inventor: Harry Duane Romo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 520 days.

(21) Appl. No.: 17/773,999

(22) PCT Filed: Nov. 4, 2020

(86) PCT No.: PCT/US2020/058924
§ 371 (c)(1),
(2) Date: May 3, 2022

(87) PCT Pub. No.: WO2021/092041
PCT Pub. Date: May 14, 2021

(65) Prior Publication Data
US 2022/0378645 A1 Dec. 1, 2022

Related U.S. Application Data

(60) Provisional application No. 62/930,116, filed on Nov. 4, 2019.

(51) Int. Cl.
A61H 1/02 (2006.01)
A61F 5/02 (2006.01)
B25J 9/00 (2006.01)

(52) U.S. Cl.
CPC .......... A61H 1/0281 (2013.01); A61F 5/028 (2013.01); B25J 9/0006 (2013.01);
(Continued)

(58) Field of Classification Search
CPC .......... A61H 1/0281; A61H 2201/0192; A61H 2201/1614; A61H 2201/1619;
(Continued)

(56) References Cited

U.S. PATENT DOCUMENTS 1,532,304 A * 4/1925 Cunning ................. A61F 5/026
2/45
8,641,782 B2 2/2014 Kim et al.
(Continued)

FOREIGN PATENT DOCUMENTS

BR 112019026825 A2 6/2020
CN 101909555 A 12/2010
(Continued)

OTHER PUBLICATIONS

Nycz, et al., "Design and Characterization of a Lightweight and Fully Portable Remote Actuation System for Use With a Hand Exoskeleton," IEEE Robotics and Automation Letters. vol. 1, No. 2, Jul. 1, 2016, pp. 976-983.
(Continued)

Primary Examiner — Victoria Murphy
Assistant Examiner — Kris Hanyu Gong
(74) Attorney, Agent, or Firm — Workman Nydegger

(57) ABSTRACT

An interface system includes a support belt, a strap assembly, and a frame system. The frame system includes a first frame member and a second frame member. The first frame member and the second frame member each respectively have an upper attachment portion configured to have an assistive device attached thereto at a first shoulder mount assembly and a second shoulder mount assembly, respectively. The first frame member and the second frame member are each respectively connected to the strap assembly and extend downward contouring laterally and connecting to the support belt. The first frame member and the second
(Continued)

frame member contour laterally in opposed directions. The first frame member is connected posteriorly to the second frame member through a pair of hinge arms joined at a pivot connection.

19 Claims, 17 Drawing Sheets

(52) U.S. Cl.
CPC ............... *A61H 2201/0192* (2013.01); *A61H 2201/1614* (2013.01); *A61H 2201/1619* (2013.01); *A61H 2201/1623* (2013.01); *A61H 2201/1628* (2013.01); *A61H 2201/1638* (2013.01); *A61H 2201/165* (2013.01); *A61H 2201/1676* (2013.01)

(58) Field of Classification Search
CPC .... A61H 2201/1623; A61H 2201/1628; A61H 2201/1638; A61H 2201/165; A61H 2201/1676; A61F 5/028; A61F 5/02; A61F 5/026; B25J 9/0006
See application file for complete search history.

(56) References Cited

U.S. PATENT DOCUMENTS

| | | | |
|---|---|---|---|
| 9,750,632 B1* | 9/2017 | Logan | A61F 5/028 |
| 9,889,554 B2 | 2/2018 | Van Engelhoven et al. | |
| 10,736,809 B2 | 8/2020 | Cempini et al. | |
| 10,918,559 B2 | 2/2021 | Romo et al. | |
| 11,007,107 B2 | 5/2021 | Zoso et al. | |
| 2003/0223844 A1 | 12/2003 | Schiele et al. | |
| 2011/0046529 A1 | 2/2011 | Vollbrecht et al. | |
| 2018/0303699 A1 | 10/2018 | Romo et al. | |
| 2018/0361565 A1 | 12/2018 | Angold et al. | |
| 2019/0240102 A1* | 8/2019 | Genani | A61H 1/0281 |
| 2020/0038219 A1 | 2/2020 | Mizera et al. | |
| 2020/0139537 A1 | 5/2020 | Moise et al. | |
| 2020/0375834 A1 | 12/2020 | Zoso et al. | |
| 2021/0125682 A1 | 4/2021 | Sato | |
| 2021/0154084 A1 | 5/2021 | Romo et al. | |

FOREIGN PATENT DOCUMENTS

| | | |
|---|---|---|
| CN | 107930032 A | 4/2018 |
| CN | 108500957 A | 9/2018 |
| CN | 108553266 A | 9/2018 |
| CN | 108839006 A | 11/2018 |
| CN | 109318217 A | 2/2019 |
| CN | 109760021 A | 5/2019 |
| CN | 110167726 A | 8/2019 |
| CN | 110181485 A | 8/2019 |
| CN | 110678156 A | 1/2020 |
| CN | 110944804 A | 3/2020 |
| EP | 3614989 A1 | 3/2020 |
| EP | 3655198 A1 | 5/2020 |
| JP | 2009268839 A | 11/2009 |
| KR | 20200031569 A | 3/2020 |
| MX | 2019012562 A | 12/2019 |
| WO | 2016187275 A1 | 11/2016 |
| WO | 2017157941 A1 | 9/2017 |
| WO | 2018224175 A1 | 12/2018 |
| WO | 2019081851 A1 | 5/2019 |
| WO | 2020021719 A1 | 1/2020 |

OTHER PUBLICATIONS

Wei, et al., "Design on the Bowden Cable-Driven Upper Limb Soft Exoskeleton," Applied Bionics and Biomechanics, vol. 2018, Article ID 1925694, Jul. 17, 2018, 10 pages, retrieved from https://www.hindawi.com/journals/abb/2018/1925694/.

"Comau Mate: wearable technology at the service of workers," YouTube, uploaded by Comau, Jun. 19, 2018, https://www.youtube.com/watch?v=4Poz5GzaNP8.

Francis, "Comau launches 'lightweight, wearable' exoskeleton for workers," Robotics and Automation News.com, Sep. 27, 2018, 3 pages, retrieved from https://roboticsandautomationnews.com/2018/09/27/comau-launches-lightweight-wearable-exoskeleton-for-workers/19265/.

Greenfield, "New exoskeleton enters industrial wearable market," Packaging World.com, Oct. 10, 2018, 2 pages, retrieved from https://www.packworld.com/home/article/13278772/new-exoskeleton-enters-industrial-wearable-market#next-slide.

"Mate-XT Exoskeleton User's Handbook," https://mate.comau.com/application-cases/#mate-downloads, Dec. 1, 2018, 64 pages.

International Search Report and Written Opinion from corresponding PCT Application No. PCT/US2020/058924, Feb. 15, 2021.

Chinese Office Action from Corresponding Chinese Patent Application No. CN202080075993.2, Dec. 23, 2024.

* cited by examiner

INTERFACE FOR AN EXOSKELETON

CROSS-REFERENCE TO RELATED APPLICATIONS

This application incorporates by reference: U.S. Provisional Application 63/091,022, filed on Oct. 13, 2020; U.S. Provisional Application 62/489,618, filed on Apr. 25, 2017; U.S. Provisional Application 62/583,140, filed on Nov. 8, 2017; U.S. Provisional Application 62/590,844, filed on Nov. 27, 2017; U.S. Provisional Application 63/069,985, filed on Aug. 25, 2020; U.S. Pat. No. 9,572,705, granted Feb. 21, 2017; U.S. Pat. No. 8,657,769, granted Feb. 25, 2014; U.S. Pat. No. 8,172,779, granted May 8, 2012; U.S. Patent Application Publication 2016/0250061, published on Sep. 1, 2016; U.S. Patent Application Publication 2018/0303699, published on Oct. 25, 2018; and International application No. PCT/IB2020/053821, filed Apr. 22, 2020.

FIELD OF THE DISCLOSURE

The disclosure relates to an exoskeleton including actuators and/or an interface therefor, and an exoskeleton intended to assist in performing tasks while minimizing interference with a user's motion.

BACKGROUND

Wearable industrial exoskeletons, including actuators and body interfaces cooperating therewith, are an increasingly important field of technology, as exoskeletons can help users conduct various activities in a safer, more efficient, and more comfortable manner. In certain manufacturing settings, workers must conduct physically demanding and precise tasks involving heavy and/or dangerous objects and/or awkward or precarious positions, often repetitively and for hours at a stretch.

Without an exoskeleton's assistance, workers may become tired or uncomfortable, leading to errors, low productivity, and possibly even injury. Exoskeletons may also enable aging workers with valuable skills and experience to continue to work in a physically demanding field for a longer period than might be otherwise possible. Proper use of exoskeletons may prevent ergonomically improper working conditions from developing after years of work into long-term and possibly debilitating health problems for workers.

Exoskeletons are useful for supplementing a human body's natural strength and motions to provide strength, support, and comfort. Exoskeleton devices may have an independent power supply or passive or energy-storage device, enabling the exoskeleton device to do the "heavy lifting" for a human user through the function of actuators or other motion-assistive components. For example, an exoskeleton device may help a user steadily hold a heavy tool to focus their attention on using the tool to perform precision and/or repetitive work.

Exoskeletons may be configured to provide relief when a human user is working in an uncomfortable position or can improve posture. A surgeon may benefit from an exoskeleton device that relieves the surgeon of the effort of holding their arms in a certain position over a patient throughout a surgical operation or that helps the surgeon to lean over a patient in what would otherwise be an awkward or uncomfortable position for extended periods without fatigue or discomfort.

A manufacturing technician may benefit from an exoskeleton device holding their arms up or maintaining their posture as they work on a piece of equipment, especially when the technician performs work in an awkward or uncomfortable position, such as standing underneath the piece of equipment. This may be applicable for automotive manufacturing contexts, where a worker may stand underneath a car and perform tasks thereon, with their arms raised above their head.

Other beneficial arrangements include providing additional sets of hands, improved balance, strengthened grip, stabilization or locking of movements, shock absorption, muscle memory, and others.

Exoskeletons may be utilized in various environments, such as on manufacturing floors, in repair shops, or outdoors and/or in rugged environments. For example, an exoskeleton may be used in construction, agricultural, logging, nautical, maintenance, recreational, or other outdoor activities. A user may utilize a passive, assistive exoskeleton to facilitate certain construction-related tasks such as lifting, placing, and holding heavy objects and/or performing tasks in awkward positions or for uncomfortably long periods.

A user may use a passive, assistive exoskeleton in agricultural tasks such as bending or stooping to harvest produce, more safely and precisely cut trees, manipulate heavy objects and equipment on a ship, or perform landscaping-type activities. A user may don an exoskeleton device for performing aircraft maintenance at an airport. A user may utilize an exoskeleton in a warehouse or fulfillment center where the user must retrieve, gather, organize, or otherwise manipulate products on shelves, vehicles, and boxes.

Wearable exoskeleton technologies can improve endurance, precision, and safety in numerous settings, including industrial settings such as automotive manufacturing. These exoskeletons increase industrial productivity and prevent common workplace injuries by minimizing muscles and connective tissues' overuse. Exoskeletons can support and augment an operator during strenuous activities, including lifting, stooping, bending, squatting, and overhead work, to reduce employee fatigue and workplace injuries.

Exoskeletons may additionally be valuable in repetitive and/or awkward activities. An exoskeleton may be arranged to transfer loads through the exoskeleton to the ground in standing or kneeling positions and allow operators to use heavy tools as if they were weightless. Assisted by an exoskeleton, operators can effortlessly hold heavy hand tools, increasing productivity and precision by reducing muscle fatigue. Older workers with valuable experience and intuition may, through an exoskeleton system, be able to work longer than they otherwise could in physically demanding or challenging jobs.

SUMMARY

An interface system for an exoskeleton is provided. According to one embodiment, the interface system includes a support belt, a strap assembly, and a frame system with a first frame member. The first frame member has an upper attachment portion configured to have a first assistive device attached thereto at a shoulder mount assembly. The first frame member is connected to the strap assembly and extends from a user's left or right scapula downward, contouring laterally and connecting to the support belt.

According to another embodiment, the interface system includes a support belt, a strap assembly, and a frame system that includes a first frame member and a second frame member. The first frame member has an upper attachment portion configured to have a first assistive device attached thereto at a first shoulder mount assembly. The second frame member has an upper attachment portion configured to have a second assistive device attached thereto at a second shoulder mount assembly. The first frame member is connected to the strap assembly and extends downward, contouring laterally and connecting to the support belt. The second frame member is connected to the strap assembly and extends downward, contouring laterally and connecting to the support belt. The first frame member and the second frame member contour laterally in opposed directions. The first frame member is connected posteriorly to the second frame member through a pair of hinge arms joined at a pivot connection.

According to another embodiment, an exoskeleton assistive system is provided. The exoskeleton assistive system includes an interface system, a first assistive device attached to the interface system, and a second assistive device attached to the interface system. The interface system includes a support belt, a strap assembly, and a frame system that includes a first frame member and a second frame member. The first frame member has an upper attachment portion to which the first assistive device is connected at a shoulder mount assembly. The second frame member has an upper attachment portion to which the second assistive device is connected at a shoulder mount assembly. The first frame member is connected to the strap assembly and extends downward, contouring laterally and connecting to the support belt. The second frame member is connected to the strap assembly and extends downward, contouring laterally and connecting to the support belt. The first frame member and the second frame member contour laterally in opposed directions. The first frame member is connected posteriorly to the second frame member through a pair of hinge arms joined at a pivot connection.

Figure 1A:
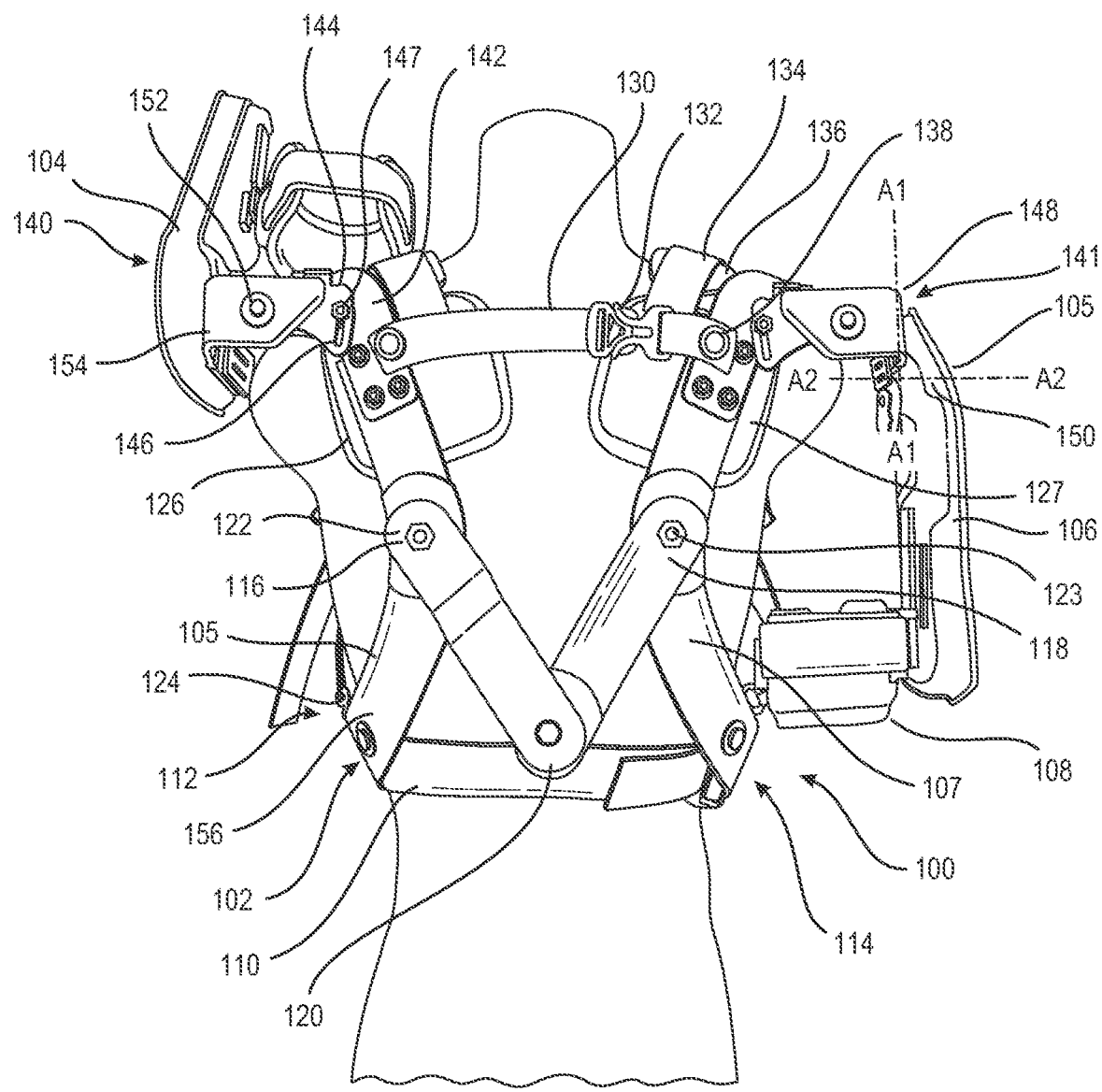
FIG. 1A is a schematic posterior view of an individual wearing an embodiment of an exoskeleton interface system.

The drawing figures are not drawn to scale, but instead are drawn to provide a better understanding of the components and are not intended to be limiting in scope, but to provide exemplary illustrations.

DETAILED DESCRIPTION OF VARIOUS EMBODIMENTS

A. Overview

A better understanding of the disclosure's different embodiments may be had from the following description read with the accompanying drawings in which like reference characters refer to like elements.

While the disclosure is susceptible to various modifications and alternative constructions, certain illustrative embodiments are in the drawings described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an exoskeleton interface system and variants as disclosed, a description of a few terms is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Last, the term "anterior" has its ordinary meaning and refers to a location ahead of or to the front of another location.

These anatomical terms follow the user wearing the exoskeleton interface system, referring to an anatomical position. An anatomical position is generally defined as the erect position of the body with the face directed forward, the arms at the side, and the palms of the hands facing forward, and which is a reference in describing the relation of body parts to one another.

The terms "rigid," "flexible," "compliant," and "resilient" may distinguish characteristics of portions of certain features of the exoskeleton interface system. The term "rigid"

should denote that an element of the exoskeleton interface system, such as a frame, is generally devoid of flexibility. Within the context of features that are "rigid," it should indicate that they do not lose their overall shape when force is applied and may break if bent with sufficient force. The term "flexible" should denote that features are capable of repeated bending such that the features may be bent into retained shapes or the features retain no general shape but continuously deform when force is applied.

The term "compliant" may qualify such flexible features as generally conforming to another object's shape when placed in contact therewith, via any suitable natural or applied forces, such as gravitational forces or forces applied by external for example, strap mechanisms. The term "resilient" may qualify such flexible features as generally returning to an initial general shape without permanent deformation. As for the term "semi-rigid," this term may connote properties of support members or shells that provide support and are free-standing; however, such support members or shells may have flexibility or resiliency.

The disclosure's embodiments are adapted for a human body and may be dimensioned to accommodate different types, shapes, and sizes of human body sizes and contours. For explanatory purposes, the exoskeleton interface system embodiments described correspond to different body sections and are denoted by general anatomical terms for the human body.

The exoskeleton interface system's embodiments may correspond to anterior and posterior body sections defined by an anterior-posterior plane. The anatomical terms described are not intended to detract from the normal understanding of such terms as readily understood by ordinary skill in the art of orthopedics, braces, human interfaces, and supports.

B. Related Art Exoskeleton Interface

Figure 9:
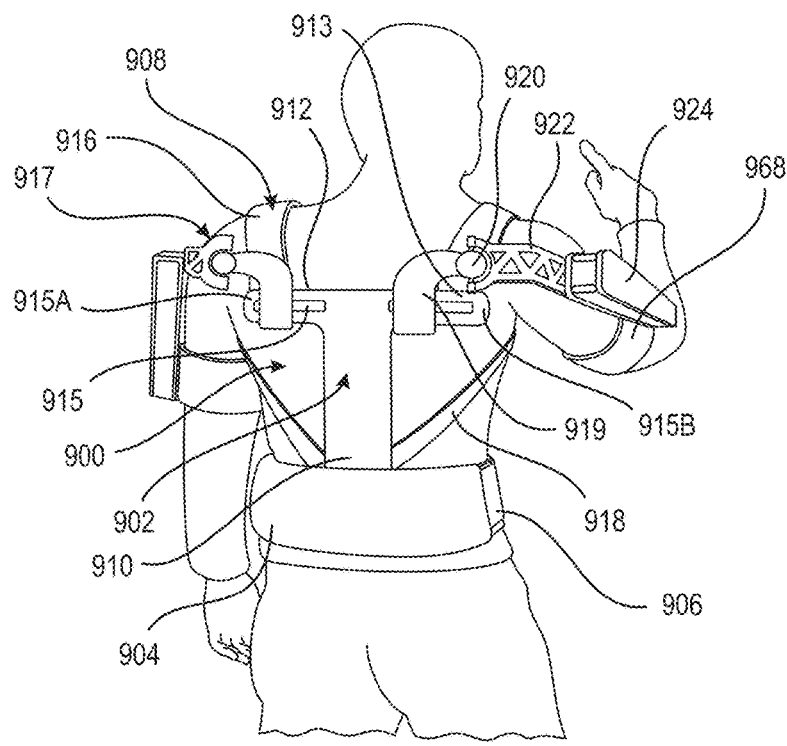
FIG. 9 is a schematic posterior view of an individual wearing an interface system and an assistive device according to related art.
Figure 10:
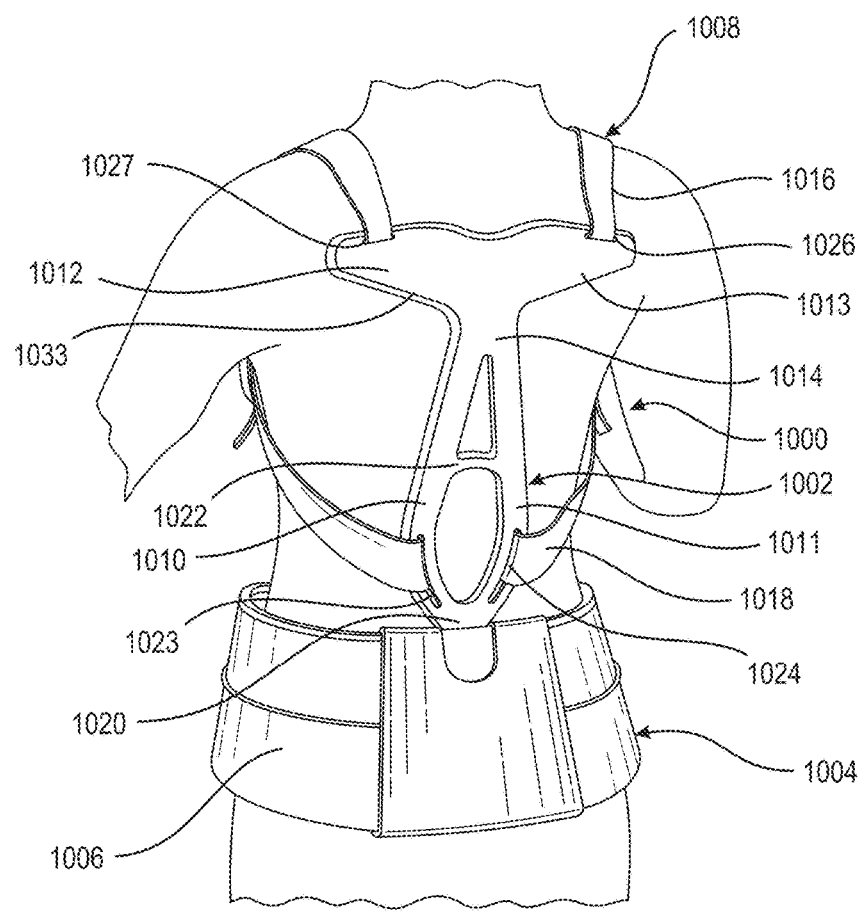
FIG. 10 is a rear perspective view of another interface system of related art.

For an understanding of the interface system of the present disclosure, reference is made to the related interface system discussed in U.S. Patent Application Publication 2018/0303699 and illustrated by convenience in FIGS. 9 and 10.

FIG. 9 shows a schematic posterior view of an individual wearing an interface system 900 and a shoulder assistive device 917 according to the related art. The interface system 900 includes a "T-shaped" posterior strut 902 extending from a shoulder strap assembly 908 to a base support 904. The T-shaped posterior strut 902 has a centrally aligned, vertical member 910 and opposed horizontal strut component or transverse members 912, 113 extending from an upper end of the vertical member 910, and arranged perpendicularly and horizontally relative to the direction of the vertical member 910. The transverse members 912, 913 are arranged to extend over a user's left and right scapula generally.

FIG. 9 further shows an assistive device 917 with support frames 919 attached to each of the free end portions 915A, 915B of the transverse members 912, 913 via horizontal slots or connection elements or defined by the transverse members 912, 913. The support frames 919 may include articulation devices 920 for the assistive device 917 and connectors 922 for attaching to a first segment 916 of a strap assembly 908. The connectors 922 may be extended vertically along the user's upper back and over the shoulder to the anterior side. The connectors 922 may comprise a rigid or semi-rigid frame. Assist mechanisms 924 are supported by the connectors 922 for offering mechanized assistance for lifting/flexion by the shoulders, which may include an actuator mechanism to provide humeral flexion assistance.

FIG. 10 shows another interface system 1000 of the related art having a centrally aligned, monolithic, T-shaped posterior strut 1002 forming an ergonomic shape with the thoracic anatomy lumbar vertebrae. The base support 1004 connects to the posterior strut 1002 and has belt segments 1006, as in preceding embodiments. A shoulder strap assembly 1008 likewise secures the interface system 1000, and connects to the posterior strut 1002 from the transverse members 1012, 1013. At least the posterior strut 1002 is lined with padding 1033, and may be covered with fabric, coatings, or other materials.

C. Embodiments of the Interface System

Figure 7:
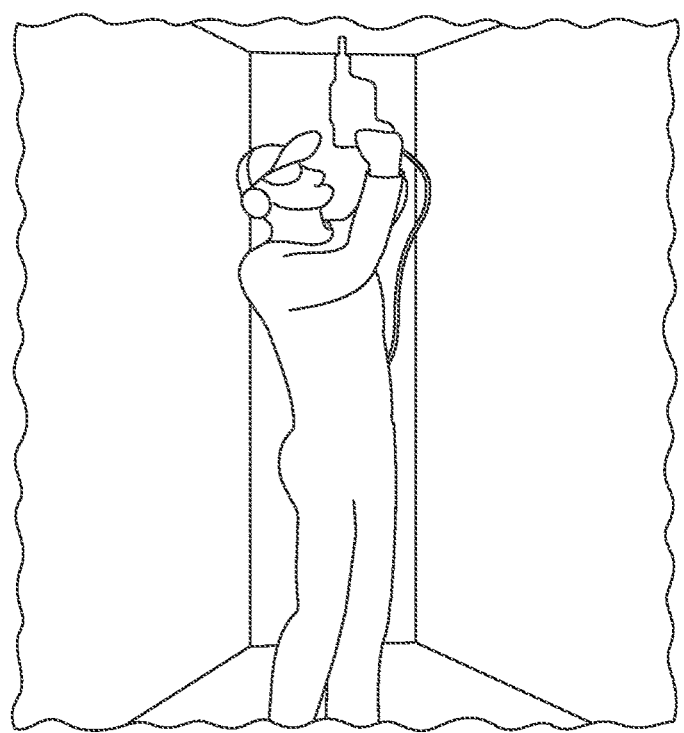
FIG. 7 shows an exemplary overhead task.

This system described herein is an exoskeleton interface system, particularly a shoulder exoskeleton or interface therefor, intended to provide flexion assistance for overhead tasks, such as the one illustrated in FIG. 7 while interfering only minimally with the motion of the user. In one embodiment, for example, as shown in FIG. 3B, the configuration is short enough to leave the lumbar spine unimpeded for the mobility of the full range of motion while engaged in activity. While discussed in the context of an exoskeleton, the principles and embodiments herein may be extended to the general field of orthopedic braces and supports or prosthetic applications.

Functional optimization of an exoskeleton involves many factors, including optimizing the exoskeleton's weight, the assistance offered, and stabilization. Design parameters must be configured so that the user does not perceive the device as a hindrance, leading to rejection, lack of adoption, or non-compliant use. To encourage adoption, factors such as bulk, pressure on the skin, heat transfer, comfort, and unintended motion restrictions must be considered.

A user's perception of comfort is user-specific and multifactorial, making it a particular challenge for functional optimization and design. User comfort includes interface pressure, location of pressure points, and the ability to dissipate heat efficiently. Relating to heat dissipation, a significant problem with existing exoskeletons that the present inventor has identified is that manual labor requires extensive musculature use, which helps generate heat. The body uses sweat to transfer heat away from the body, but an exoskeleton can block perspiration. Thus, even if the exoskeleton reduces the work required by the target musculature to zero, the user could become uncomfortably hot. Such is the case with the related art interface system shown in FIGS. 9 and 10, which include the T-shaped strut configured to provide contact against the user's torso from the upper portions of the transverse members 912, 913, to the base support 904.

Body temperature becomes particularly important in automotive manufacturing settings where the work is demanding, repetitive, and carried out in buildings with minimal or no air conditioning. Existing modalities to accomplish heat transmission include incorporating air channels in raised 3D areas, adding perforations in the frame, or using spacer textiles. While effective in their own sphere, these methods are innately limited due to the user's clothing being trapped against the skin. Regardless of the textile in use, any contact with the exoskeleton frame reduces the potential cooling through evaporation.

However, minimizing the coverage by an exoskeleton of the user's surface area is difficult because of the requirement to not exceed the skin pressure, which leads to discomfort or injury. Additionally, some superficial regions of the body are more pressure-tolerant than others. Similarly, deep structures in the body are very intolerant of such pressures.

Another problem with existing exoskeletons identified by the present inventor is providing necessary assistive forces, such as at the user's arms when performing overhead tasks, without impeding the user's ability to move, as necessary. For example, certain existing devices, such as the interface of FIGS. 9 and 10, can impede the user's ability to freely bend at the waist, which interferes with the user's ability to perform the entire range of tasks that may be necessary when wearing and using the exoskeleton.

Existing exoskeletons, such as the interface of FIGS. 9 and 10, are provided with adjustment modalities configured to position actuation elements and frame members based on the user's unique dimensions. For example, existing devices may provide sliding tracks and other mechanisms for positioning the actuators proximate to the user's musculature, such as the user's shoulders, but such mechanisms may add weight and bulk that decrease the user's comfort when using the exoskeleton. Additionally, existing exoskeletons, such as the interface of FIGS. 9 and 10, may be unable to adapt to all of the user's different dimensions, making use of the exoskeleton difficult for particular users. The adjustment modalities may also be difficult to use.

Similarly, an unsolved problem is how to secure the exoskeleton about the user in a convenient and specific manner to the user's dimensions. Many exoskeletons feature a belt that extends circumferentially about the user's torso, but adjusting the belt to conform comfortably and effectively to the user's dimensions remains difficult, as sliding or shifting of the exoskeleton frame relative to the belt often occurs. This forces the user to readjust the belt and/or the frame frequently.

A further problem, identified by the inventor, of existing exoskeleton devices, such as the interface of FIGS. 9 and 10, is that they are provided for both sides of a user's body, for example, for assisting both the left and right shoulders or the left and right legs. A user suffering from an injury to a single side of their body, such as their right shoulder, may be ill-served by an exoskeleton that assists at both shoulders, as such as device can have unnecessary bulk, unnecessarily restrict motion at the uninjured limb or side of the user's body, and be undesirable to wear in daily activities.

Another problem of existing exoskeletons that has been identified by the inventor of the present application is that existing devices only assist a single type or degree of motion. Human joints are overly complex and involve motion through multiple planes. For example, the shoulder may move through flexion/extension, abduction/adduction, internal rotation, external rotation, and circumduction movements. Existing exoskeletons for the shoulder are geared to assist in extension Existing exoskeletons likewise locate actuators proximate the musculature to which the exoskeleton provides assistive forces. For example, actuators may be provided proximate the user's shoulders, such as at the upper arms, to provide assistive forces for extending the user's arms above their head. Locating the actuators at the upper arms can add to the exoskeleton's bulk and weight, reducing the comfort and convenience of using the exoskeleton.

Given the preceding discussion, there is a need for an improved exoskeleton that improves user comfort, compliance, and effectiveness of the assistance offered while minimizing the drawbacks of existing exoskeletons, including the problems of exoskeletons impeding the movement of the user, being poorly adapted to accommodate the unique dimensions of the user, and the problem of exoskeletons assisting in a single range of motion, necessarily providing assistance at both sides of a user's body and necessarily providing actuators proximate the musculature to which assistance is to be provided.

Exoskeleton embodiments of the present disclosure advantageously address the drawbacks and problems of existing exoskeletons identified by the inventor and provide an exoskeleton, including a frame system and actuators that assist a user minimizing the interference of the exoskeleton with the user's normal motions. Exoskeleton embodiments, comprising actuators and a frame, advantageously reduce heat buildup, allow for movement at the user's waist and lower back, provide for unilateral assistance and support, provide an improved torso belt configuration, facilitate remote assistance to the user's musculature, and provide assistance in multiple degrees of motion.

According to an embodiment, the exoskeleton embodiments minimize the contact area between the exoskeleton, allowing the user's clothing freedom to move, allowing perspiration to evaporate through air movement under the clothing. The frame of exoskeleton embodiments facilitates air movement to maximize the transmission of heat away from the body.

The exoskeleton embodiments advantageously offer desired assistance at a joint or joints, for example, while more advantageously distribute the required pressure due to the assistive devices, thus offering stabilization of torque assistance up to 6 Nm on each side for total combined torque assistance of 12 Nm, due to the user simultaneously using both arms at 6 Nm each arm. In exoskeleton embodiments for the shoulders, the exoskeleton comprises an interface that can be worn and stabilized on the torso, creating stabilizing counter forces while enabling the exoskeleton to generate and transmit assistive forces through soft tissue to the skeletal structure.

The actuators of the exoskeleton embodiments may utilize independent actuation of shoulder flexion through, for example, a spring mechanism mounted in the sagittal plane with an abduction/adduction hinge wrapping around the posterior aspect of the shoulder. The embodiments may strategically place required forces on the body in correct locations for stabilization, and that can also readily tolerate resulting pressures. Such areas may include the scapula, shoulder straps, and waist, all tolerant areas for loading.

The exoskeleton may be configured to have a minimal device weight and minimize other motions at the assisted joint or elsewhere in the body. Whereas existing exoskeletons may utilize a monolithic strut with linear bearings to facilitate bilateral mounting of spring-assist mechanisms while transferring the torque and weight of the entire assembly through the frame and to the user, the exoskeleton embodiments may comprise a frame with minimized coverage of the body to facilitate heat transmission through air exchange and cooling via perspiration.

While the exoskeleton embodiments' frame may minimize body coverage, the frame of the exoskeleton embodiments ensures that skin contact pressures are not exceeded. That is, the frame embodiments may ensure that the exoskeleton does not exert enough pressure to cause capillary closure, loss of circulation, or perceived discomfort. The frame design may be configured to transfer most loads and weights to the torso or waist at a predetermined distance from the torque generating actuators, thus resulting in small counterforces and pressures. As the exoskeleton provides an assistive flexion torque at the targeted joint, such as the shoulder, the force is transmitted from the actuator to the humerus through a soft cuff and the frame interface by counterforces to the user's body.

Figure 8:
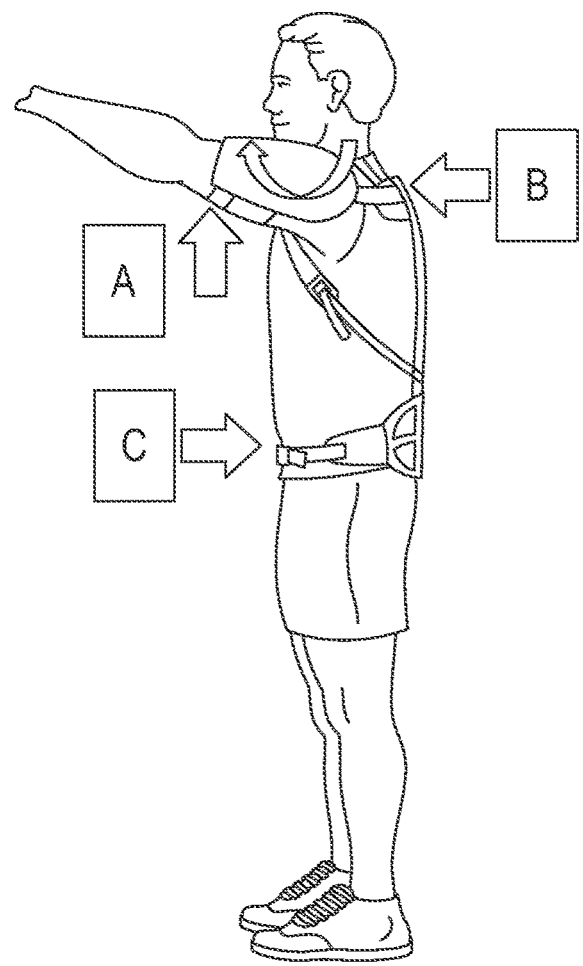
FIG. 8 shows a force diagram of an exoskeleton interface system worn by a user.

As shown in FIG. 8, a force diagram is illustrative of the problems of previous exoskeleton systems. As shown in FIG. 8 at "A," a flexion torque at the shoulder is transmitted to the humerus with a cuff pressing on the posterior aspect of the humerus/triceps. A midpoint fulcrum is located over the region of the scapulae, as shown at "B." A counterforce is produced at "C" at the anterior of the ribcage with a short frame or at the anterior waist with a long frame of the exoskeleton system. Referring to FIG. 8, the exoskeleton system offers torque assistance at the shoulder in forward flexion (shown by the curved arrow). This arrangement creates for torque "A" upon the arm. The fulcrum in the system is at the scapula (B), and the counterforce is at the anterior waist belt (C).

As noted above, a related exoskeleton interface system relied on a monolithic, T-shaped posterior strut which has horizontal members (upper portion of the "T") residing over the scapulae and extending outward from the central portion of the "T." The T-shaped strut's central portion extends down to a panel and waist belt, which affixes the system to the waist. Shoulder straps assist in sharing weight between the shoulders and the strut closely to the scapulae and shoulders. This system works well for providing shoulder flexion assistance and postural and thoracic-lumbar support of the spine. Such a system has been found by the present inventor as being perceived by users as limiting spinal motion. The present inventor has found that the rigid monolithic "T" connection between the shoulder actuators and the waist panel does not easily allow individual shoulder elevation or depression.

Accordingly, rather than a T-shaped monolithic strut centered on the spine and secured at the waist, flexion actuators on the upper, horizontal members of the "T," a first embodiment of the present disclosure, as shown FIGS. 1A-1D, includes a frame 102 for the interface 100, the frame 102 having separate left and right frame members 112, 114, which independently attach to respective left and right shoulder mount assemblies 140, 141, to which respective left and right actuators 104, 105 may be mounted. Each of the right frame member 114 and left frame member 112 extends downwardly from the point of attachment of the shoulder mount assembly and is contoured respectively around the lateral aspect of the torso of the user. The first (for example, left) frame member 112 and the second (for example, right) frame member 114 contouring laterally in opposed directions. According to this embodiment, the first (for example, left) frame member 112 and the second (for example, right) frame member 114 extend downward contouring laterally and connecting to the support belt 110 in a generally symmetric manner concerning a sagittal plane of the user.

Each right frame and left frame member begins proximally at proximal portions 142 at a respective right and left scapulae, then transitions downward and laterally through body portion 107 of the frame member, to the side of the torso where a distal end of each right frame member and left frame member attach to the support belt 110. This arrangement reproduces the basic contact points for stabilization of the frame and delivers the assistive torque to the shoulder while it entirely minimizes the contact area/coverage of the body. As shown in FIG. 8, such an interface provides contact at the scapular fulcrum point (B) and counterforce (C), which is needed for the minimal interface stabilization scheme noted above while minimizing unnecessary contact against the user, thereby increasing the efficiency of the dissipation of heat.

Figure 1B:
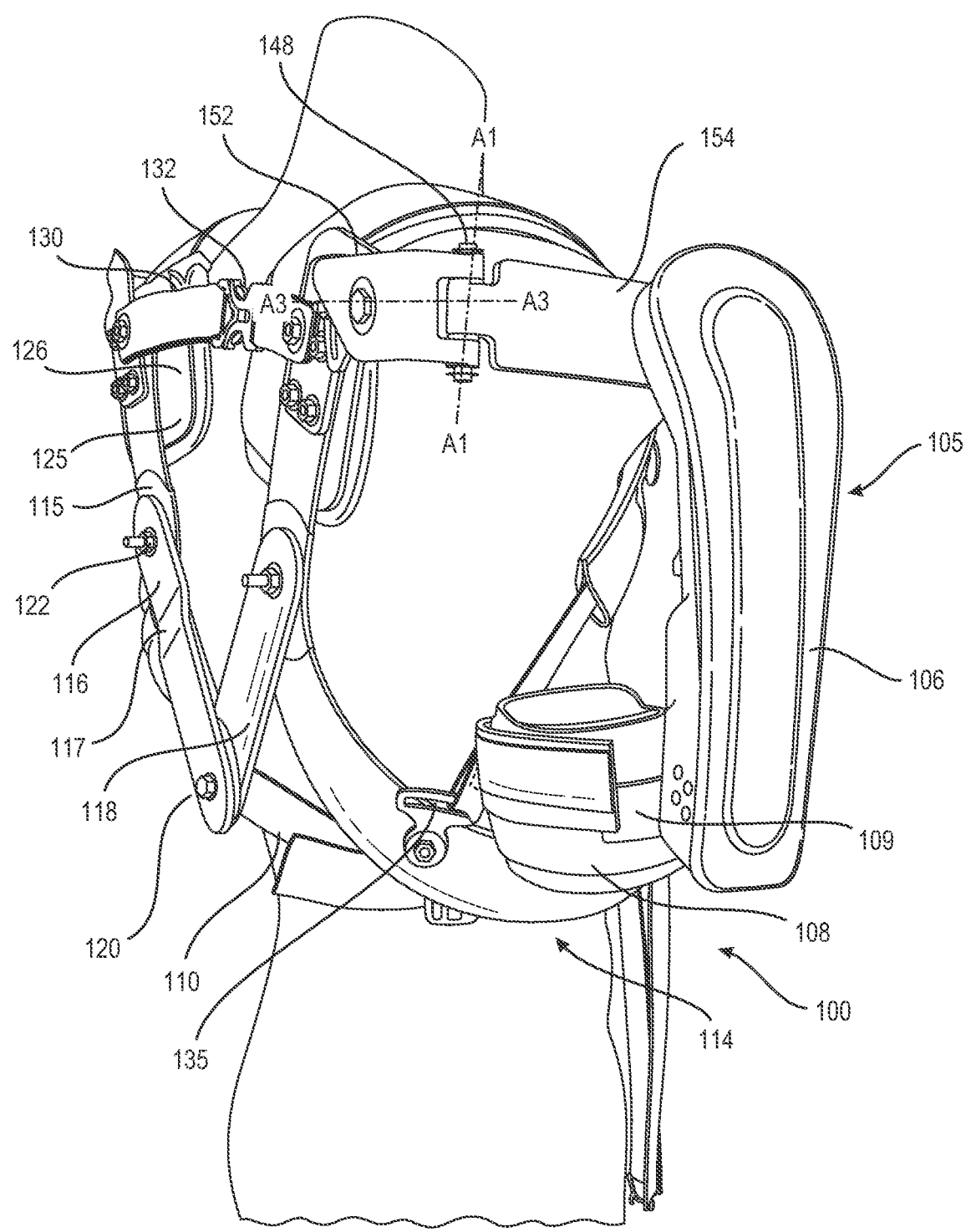
FIG. 1B is a schematic, perspective posterior-lateral view of the exoskeleton interface system according to FIG. 1A.

As further shown in the embodiment of FIG. 1A, the left frame member 112 is connected posteriorly to the right frame member 114 by a single attachment point at hinge 120 via a pair of hinge arms. In the embodiment of FIG. 1A, the hinge arms include left hinge plate 116 and right hinge plate 118. Left hinge plate 116 connects to left frame member 112 at lateral pivot point 122, and right hinge plate 118 connects to right frame member 114 at lateral pivot point 123. As shown in FIG. 1B, left hinge plate 116 may be provided with profile bend 117 to accommodate the overlaying portion of the hinge arms at a center or hinge 120. The hinge arms are joined in the center with the hinge 120 to form a 3-point linkage. The broad hinge arms of the left hinge plate 116 and right hinge plate 118 prevent torsion between the left frame member 112 and the right frame member 114 while allowing the left and right frame members 112, 114 to tilt toward or away from each other in the coronal plane.

The hinge 120 allows the left and right frame members' width to be adjusted and to move with the user. This arrangement accommodates scapular protraction and retraction. Because of both left and right frame members' independent action, the design can accommodate some shoulder elevation or depression. The hinge 120 also accommodates the shoulder/waist width of the user. The interface of the embodiment of FIG. 1A further includes an adjustable strap 130, which may include an elastic mechanism or a spring mechanism connecting an upper portion of the left frame member 112 to an upper portion of the right frame member 114 such that the adjustable strap, elastic mechanism, or spring mechanism prevents lateral separation of the upper portion of the first frame member from the upper portion of the second frame member beyond a predetermined distance in the coronal plane. Adjustable strap 130 is attached to each of the respective left and right frame members 112, 114 by respective strap attachments mechanisms 138, which are preferably pivotable. Additionally, release mechanism 132 is provided to easily release the adjustable strap 130 and provide additional and quick movement of the left frame member 112 from the right frame member 114, for example, when donning or removing the interface exoskeleton. This articulation facilitates proximal broadening or narrowing between the left and right frame members in the coronal plane and obviates the need for linear bearings (and their respective maintenance, cost, and weight).

Figure 1C:
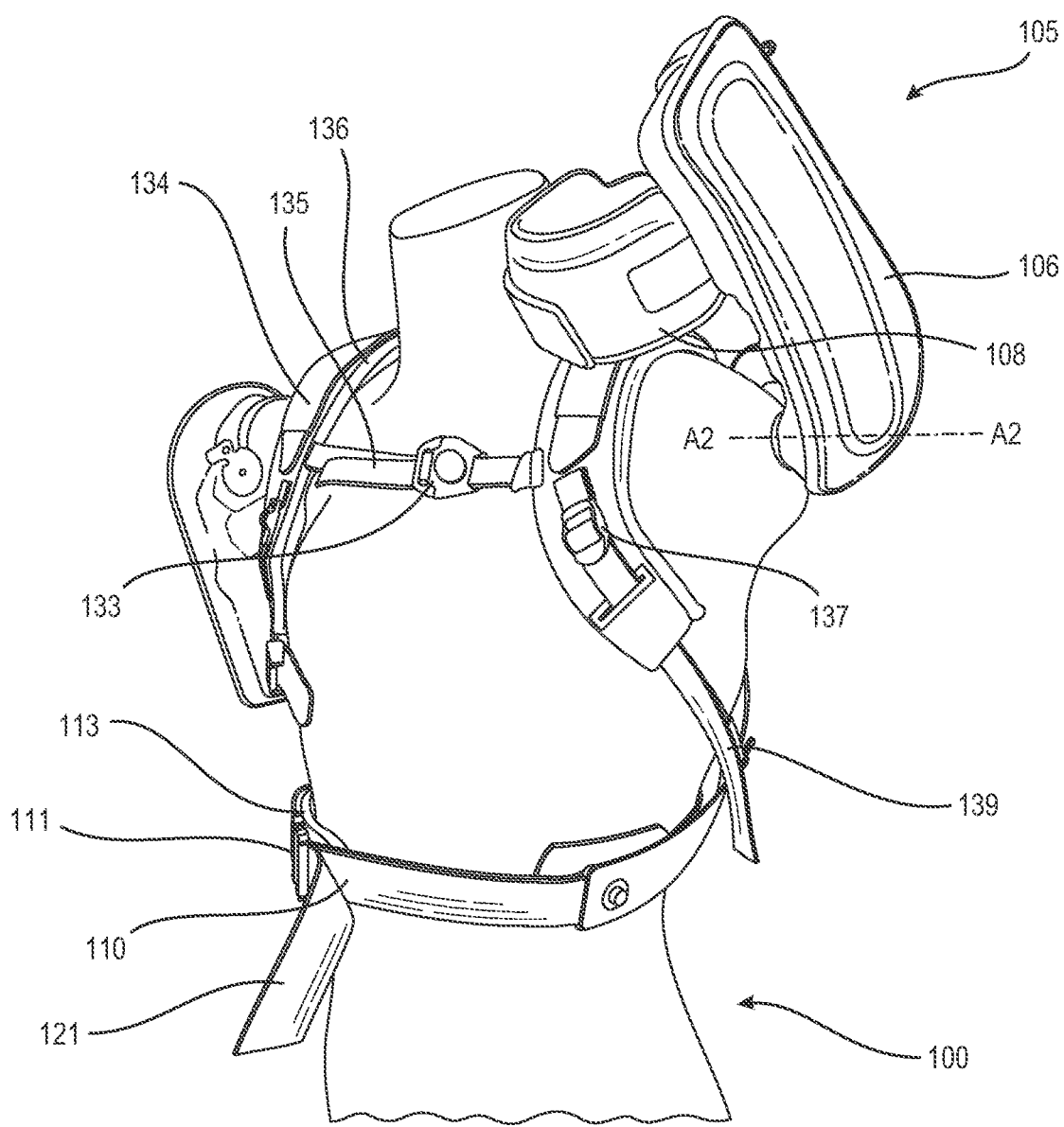
FIG. 1C is a schematic, perspective anterior-lateral view of the exoskeleton interface system according to FIG. 1A.

Once donned, the lower belt (support belt 110) affixes the distal (lower) ends of the left and right frame members to the lateral area of the user's respective left and right side of the user's trunk, as illustrated in FIGS. 1A, 1B, and 1C.

In the embodiment of FIGS. 1A-1D, the interface system further includes a strap assembly, including respective left and right shoulder straps 134, each having a shoulder pad 136. Provided at each of the upper, proximal portions of the first and second frame members, a rigid shoulder pad or scapular pad 126, 127 is provided, preferably at the user's left and right scapulae. Under each of the shoulder pad or scapular pad 126, 127, a softer, supportive material 125 is provided for more comfortable contact with the user.

Also, at or near the upper, proximal portions 142 of each of the first and second frame members 112, 114, shoulder mount assemblies 140 (left) and 141 (right) are provided that connect left and right actuators 104, 105 to the upper, proximal portions of each of the first and second frame members 112, 114. Shoulder mount assemblies 140, 141 each include a respective shoulder support plate 144 with guide pin 147 and abduction track 146, and a shoulder abduction plate 154 attached to the shoulder support plate 144 by pivot connection 152.

Accordingly, up to three degrees of movement are provided with the embodiment of FIGS. 1A-1D. Horizontal shoulder abduction and adduction are permitted by vertically-oriented rotation hinge 148 oriented along direction A1. Humeral flexion and extension are permitted by a horizontally-oriented rotation hinge 150 oriented along direction A2. Additionally, actuators 104, 105 provide humeral flexion assistance, with the arm cuffs 108 that affix to the user's humerus. Arm cuffs 108 are adjustable to accommodate a considerable size range of users' arms and adjust relative to firth changes suitable for potential users and a user's arm changes during contraction. The third degree of movement is provided due to the pivoting around direction A3, as shown, for example, in FIG. 1B, in which a shoulder abduction plate 154 is pivotably attached to the shoulder support plate 144 by pivot connection 152. Alternatively, movement about the axis of A3 may be intentionally limited by preventing travel of guide pin or fastener 147 within guide track 146. As described in the embodiment of FIGS. 5 and 6A-6B, abduction assistance may also be provided through an additional actuator assembly.

Figure 1D:
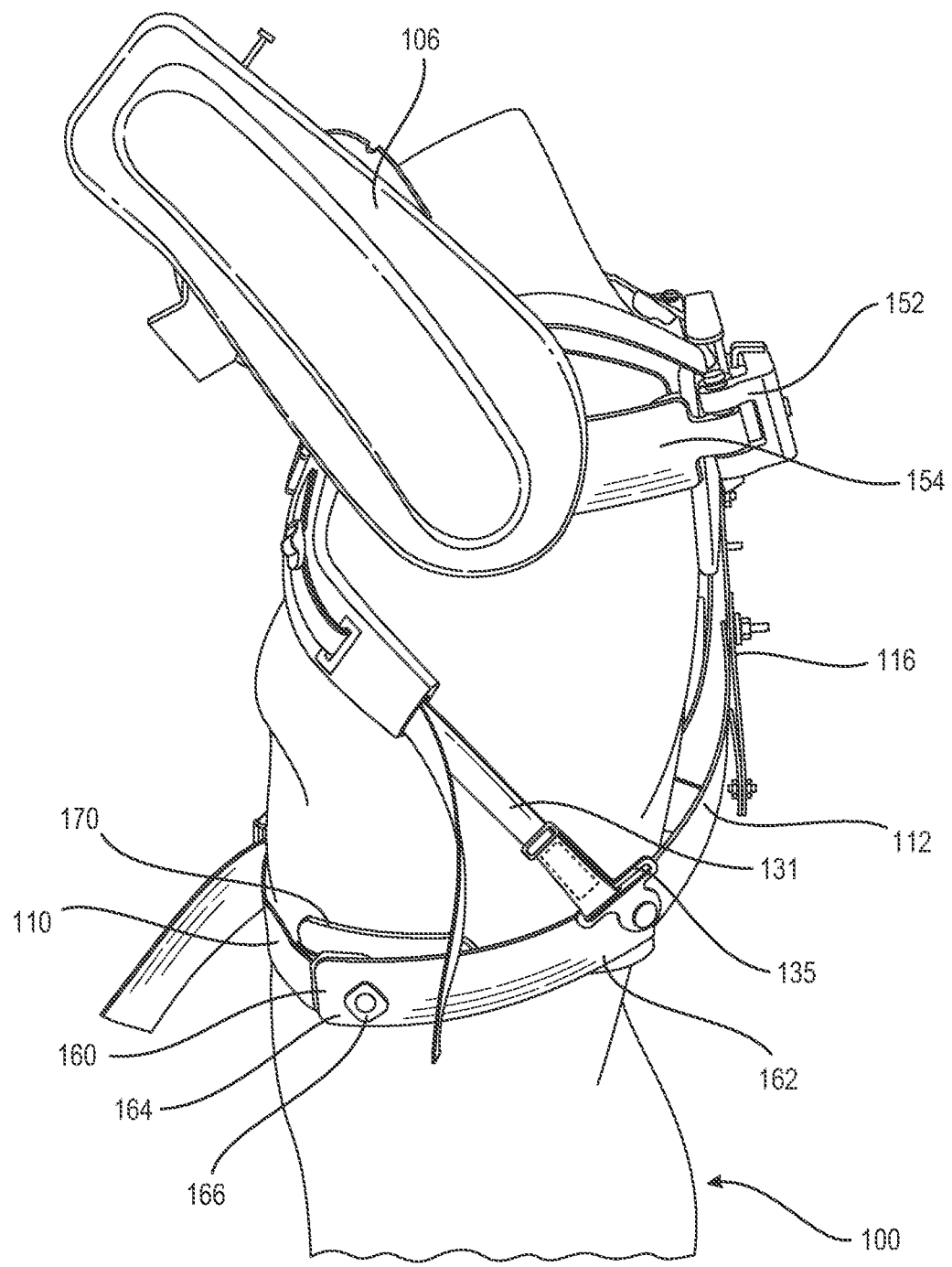
FIG. 1D is a schematic lateral view of the exoskeleton interface system according to FIG. 1A.

Each right frame and left frame member begins proximally at upper, proximal portions 142 at a respective right and left scapulae, and extends downwardly and laterally through body portion 107 of the frame member, to the side of the torso where a distal end 160 of each right frame member and left frame member respectively attach to the support belt 110. FIG. 1D shows the distal end 160 of left frame member 112 attaches to the support belt 110 by fastener 166. A lateral torso pad 170 including a rigid outer material and a softer, inner material is provided at each connection point of the left and right frame members to the support belt 110.

The interface of the embodiment of FIGS. 1A-1D further includes a strap assembly, including two shoulder straps 134 that extend over the shoulder of a user, and a connecting segment 131 that connects a lower, anterior portion of each of the shoulder straps 134 to a lower portion of the left and right frame member, respectively. Underlying shoulder strap pads 136 is provided at the shoulder segment of shoulder strap 134. Anterior chest strap 135 is provided connecting front portions of shoulder straps 134, with chest strap 135 being adjustable to accommodate various users' required chest dimensions. A chest buckle 133 is provided to unfasten the chest strap to aid in donning and removing the interface 100. The length of connecting segment 131 can be adjusted by length adjustment fastener 137 to provide more or less excess strap length 139, appropriately and comfortably fit the shoulder strap 134 to the user, and adjust for the dimensions of the user's shoulder.

Figure 3A:
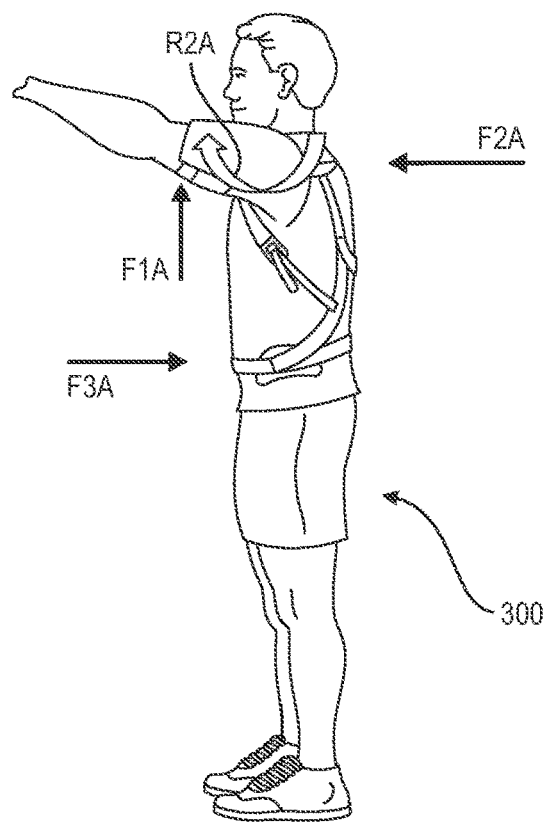
FIG. 3A shows a schematic lateral view of an embodiment of a long version of the exoskeleton interface system.
Figure 3B:
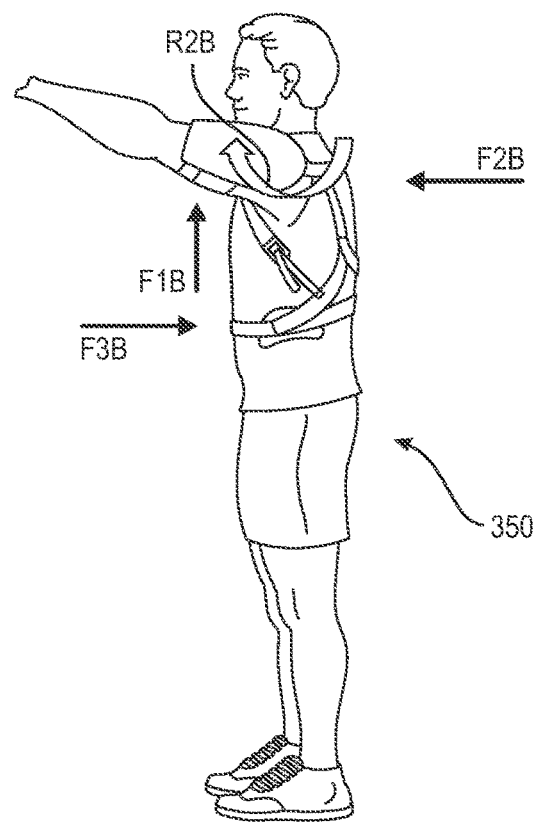
FIG. 3B shows a schematic lateral view of an embodiment of a short version of the exoskeleton interface system.

As shown in FIGS. 3A and 3B, the frame's length can be varied to extend down to the lower thoracic vertebral dimension, as shown in FIG. 3B, which leaves the lumbar vertebrae/lower back free from contact and free to move in all planes. The length could also be extended down to the iliac crest, as shown in FIG. 3A, which could also help share the weight of the device while still leaving the posterior aspect of the torso open with minimal contact while offering relatively free flexion/extension. In either case, a supportive belt, such as a thin belt, wraps around anteriorly, creating the counterforce F3A or F3B with minimal coverage of the body, and thus providing the ability to efficiently dissipate heat from the user.

At the proximal (upper) end of the frame members, the actuator mount is connected via a single rotational point over the scapula allowing abduction via a single pivot point bearing. This is also the fulcrum point "B" of the 3-point force system in FIG. 8. The scapula is protected from these loads by padding to reduce pressure to an acceptable level.

For functional/contextual purposes, the linkage to the actuator is described here because it terminates at the torque/assistance force point "A" of the 3-point force system at the posterior arm of FIG. 8. The mount wraps around the shoulder, passing across a vertically oriented hinge posterior to the glenohumeral joint facilitating internal/external rotation of the humerus and forearm, then terminating at the actuator, providing desired passive torque to the shoulder for flexion assistance. This arrangement completes the third necessary torque transmission point in the minimal 3-point force system of FIG. 8.

FIGS. 2A-2G show another embodiment of a lumber/iliac crest length interface. As mentioned above, this interface has first and second frame members extending to the user's waist. This embodiment includes anatomically formed hip pads with internal reinforcement to retain shape. These are designed to rest in the waist space between the inferior costal margin and over the wings of the ilium. The frame weight is thus transferred to the pelvis. Although lateral bending is somewhat compromised, the felt-weight (i.e., the weight perceived by the user) of the frame is reduced while the flexion/extension motion of the lumbar spine remains effectively unencumbered. The shoulder-generated loads on the frame are transferred to the anterior anatomy at a greater distance from the shoulders, so the felt-weight and load and pressure on the user's skin is reduced.

Similar to the embodiment of FIGS. 1A-1D, rather than a T-shaped monolithic strut centered on the spine and secured at the waist, flexion actuators on the horizontal members of the "T," the embodiment FIGS. 2A-2G includes a frame 202 for an interface 200, the frame 202 having separate left and right frame members 212, 214, which independently attach to respective left and right shoulder mount assemblies 240, 241, to which respective left and right actuators 204, 205 may be mounted. At the upper, proximal ends of each of the left and right frame members, a laterally-extending transverse portion 262, 264 extends outward to the respective left and right shoulder mount assemblies. From the upper transverse portions 262, 264, each of the right frame member 214 and left frame member 212, extends downwardly and is contoured respectively around the lateral aspect of the torso of the user. The first (for example, left) frame member 212 and the second (for example, right) frame member 214 contours laterally in opposed directions. According to this embodiment, the first (for example, left) frame member 212 and the second (for example, right) frame member 214 extend downward contouring laterally and connect to the support belt 210 in a general symmetric manner concerning a sagittal plane of the user. Each right frame and left frame member begins proximally at transverse portions 262, 264 at a respective right and left scapulae, then transitions downward and laterally through body portion 207 of the frame member, to the side of the torso where a distal end of each right frame member and left frame member attach to a support belt 210. This embodiment thus reproduces the basic contact points for stabilization of the frame and delivers the assistive torque to the shoulder while it entirely minimizes the contact area/coverage of the body. As shown in FIG. 8, such an interface provides contact at the scapular fulcrum point (B) and counterforce (C), which is needed for the minimal interface stabilization scheme noted above while minimizing unnecessary contact against the user thereby increasing the efficiency of the dissipation of heat.

Figure 2A:
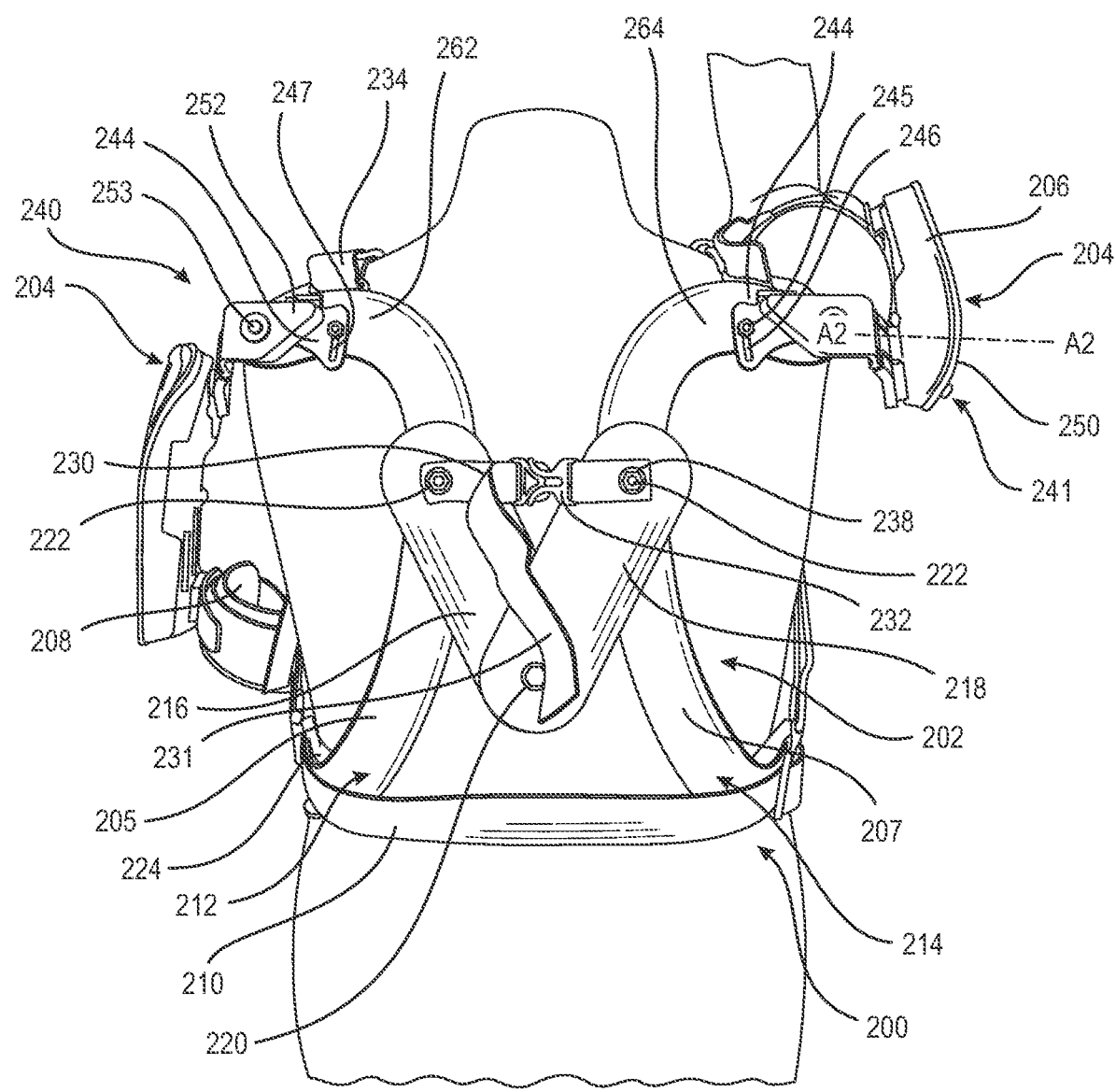
FIG. 2A is a schematic posterior view of another embodiment of an exoskeleton interface system.

As further shown in the embodiment of FIG. 2A, the left frame member 212 is connected posteriorly to the right frame member 214 by a single attachment point at a hinge 220 via a pair of hinge arms. In the embodiment of FIG. 2A, the hinge arms include left hinge plate 216 and right hinge plate 218. Left hinge plate 216 connects to left frame member 212 at lateral pivot point 222, and right hinge plate 218 connects to right frame member 214 at lateral pivot point 223. The hinge arms are joined in the center with a hinge 220 to form a 3-point linkage. The broad hinge arms of left hinge plate 216 and right hinge plate 218 prevent torsion between the left frame member 212 and the right frame member 214 while allowing the left and right frame members 212, 214 to tilt toward or away from each other in the coronal plane. The hinge 220 allows the left and right frame members' width to be adjusted and to move with the user. This configuration accommodates scapular protraction and retraction. Because of the independent action of both left and right frame members, the design can accommodate some shoulder elevation or depression. The hinge 220 also accommodates the shoulder/waist width of the user.

The interface of the embodiment of FIG. 2A further includes an adjustable strap 230, which may include an elastic mechanism or a spring mechanism connecting, connecting an upper portion of the left hinge plate 216 to an upper portion of the right hinge plate 218 between lateral pivot point 222 and lateral pivot point 223 such that the adjustable strap, elastic mechanism, or spring mechanism prevents lateral separation of the upper portion of the first frame member from the upper portion of the second frame member beyond a predetermined distance in the coronal plane. Additionally, release mechanism 232 is provided to easily release the adjustable strap 230 and provide additional and quick movement of the left frame member 212 from the right frame member 214, for example, when donning or removing the interface or exoskeleton. This articulation facilitates proximal broadening or narrowing between the left and right frame members in the coronal plane and obviates the need for linear bearings (and their respective maintenance, cost, and weight).

Once donned, the lower belt (support belt 210) affixes the distal (lower) ends of the left and right frame members to the lateral area of the user's respective left and right side at the user's trunk, as illustrated in FIGS. 1A, 1B, and 1C.

In the embodiment of FIGS. 2A-2G, the interface system further includes a strap assembly including respective left and right shoulder straps 234, each having a shoulder pad 236.

At or near the upper, laterally-extending transverse portions 262, 264 of each of the first and second frame members 212, 214, shoulder mount assemblies 240 (left) and 241 (right) are provided that connect left and right actuators 204, 205 to the upper, proximal portions of each of the first and second frame members 212, 214. Shoulder mount assemblies 240, 241 each include a respective shoulder support plate 244 with guide pin 247 and abduction track 246, and a shoulder abduction plate 254 attached to the shoulder support plate 244 by pivot connection 252.

Figure 2B:
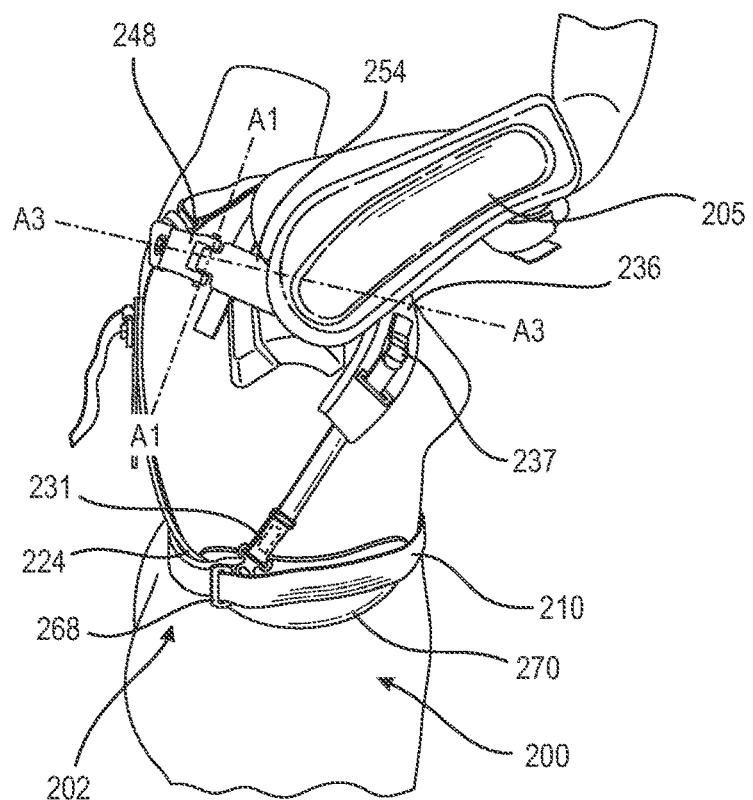
FIG. 2B is a perspective posterior-lateral view of the exoskeleton interface system according to FIG. 2A.
Figure 2C:
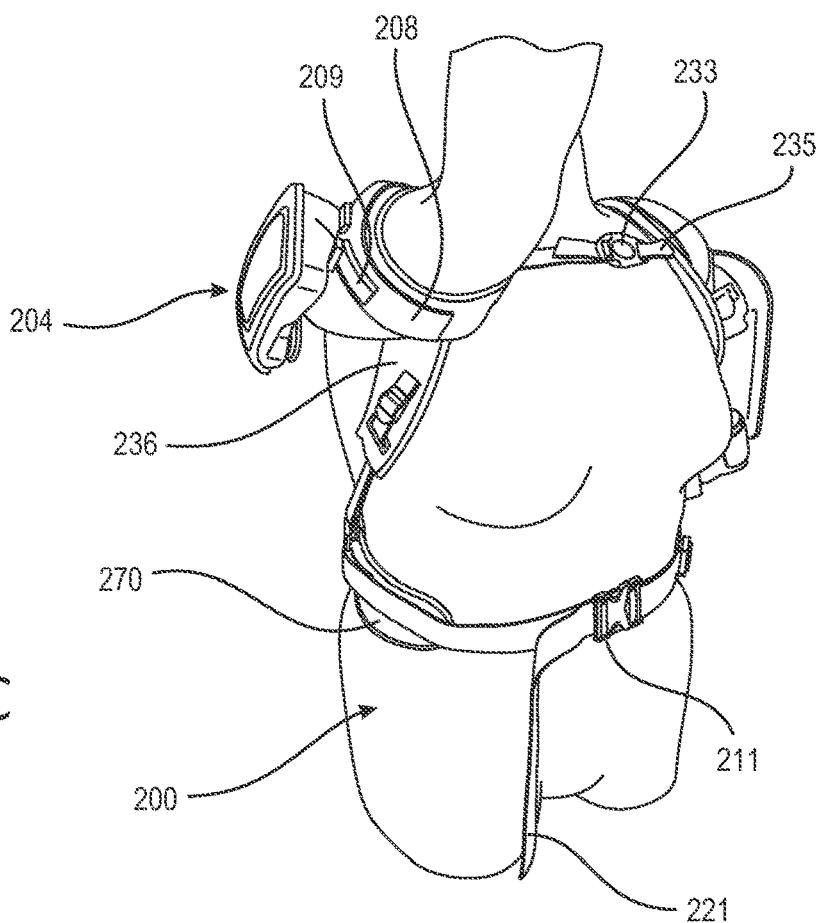
FIG. 2C is a perspective anterior-lateral view of the exoskeleton interface system according to FIG. 2A.

Accordingly, up to three degrees of movement are provided with the embodiment of FIGS. 2A-2C. Horizontal shoulder abduction and adduction are permitted by vertically-oriented rotation hinge 248 oriented along direction A1. Humeral flexion and extension are permitted by a horizontally-oriented rotation hinge 250 oriented along direction A2. Actuators 204, 205 provide humeral flexion assistance, with humeral cuff 208, which affix to the user's humerus. The arm cuffs 208 are adjustable to accommodate a considerable size range of users' arms and adjust relative to firth changes suitable for potential users and a user's arm changes during contraction. The third degree of movement is provided due to the pivoting around direction A3, as shown, for example, in FIG. 2B, in which a shoulder abduction plate 254 is pivotably attached to the shoulder support plate 244 by pivot connection 253.

Alternatively, movement about the axis of A3 may be intentionally limited by preventing travel of guide pin or fastener 247 within guide track 246. As described in the embodiment of FIGS. 5 and 6A-6B, abduction assistance may also be provided through an additional actuator assembly.

Figure 2D:
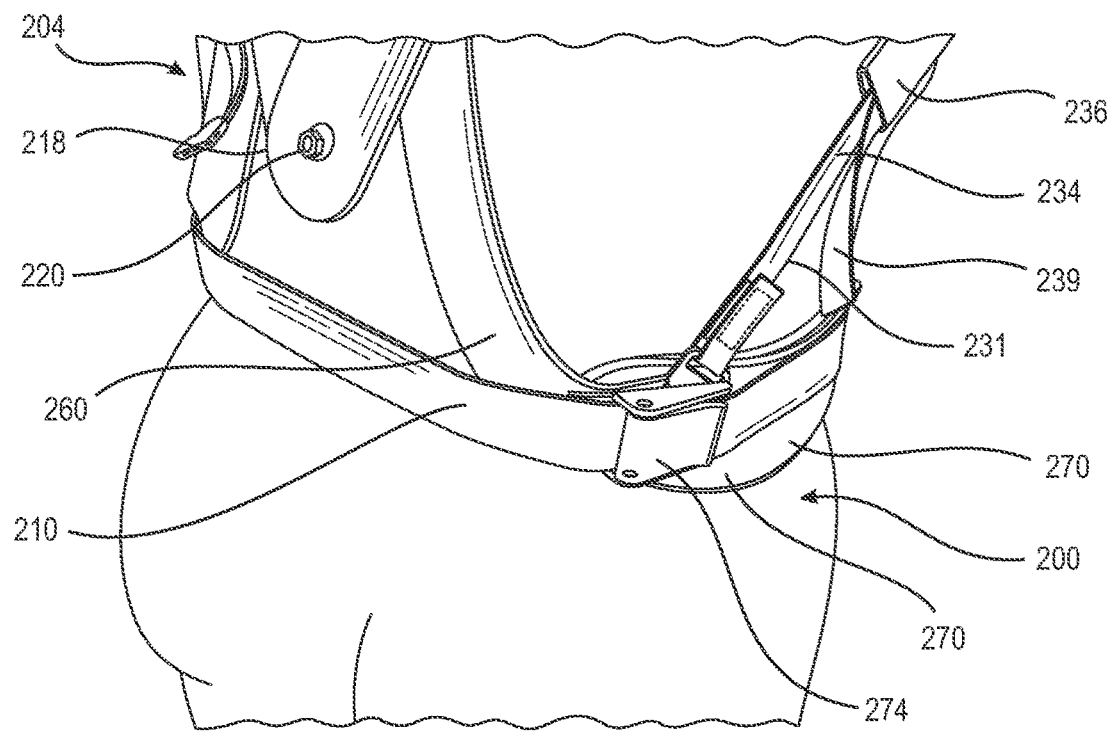
FIG. 2D is a close-up of the perspective posterior-lateral view of the exoskeleton interface system according to FIG. 2A.
Figure 2E:
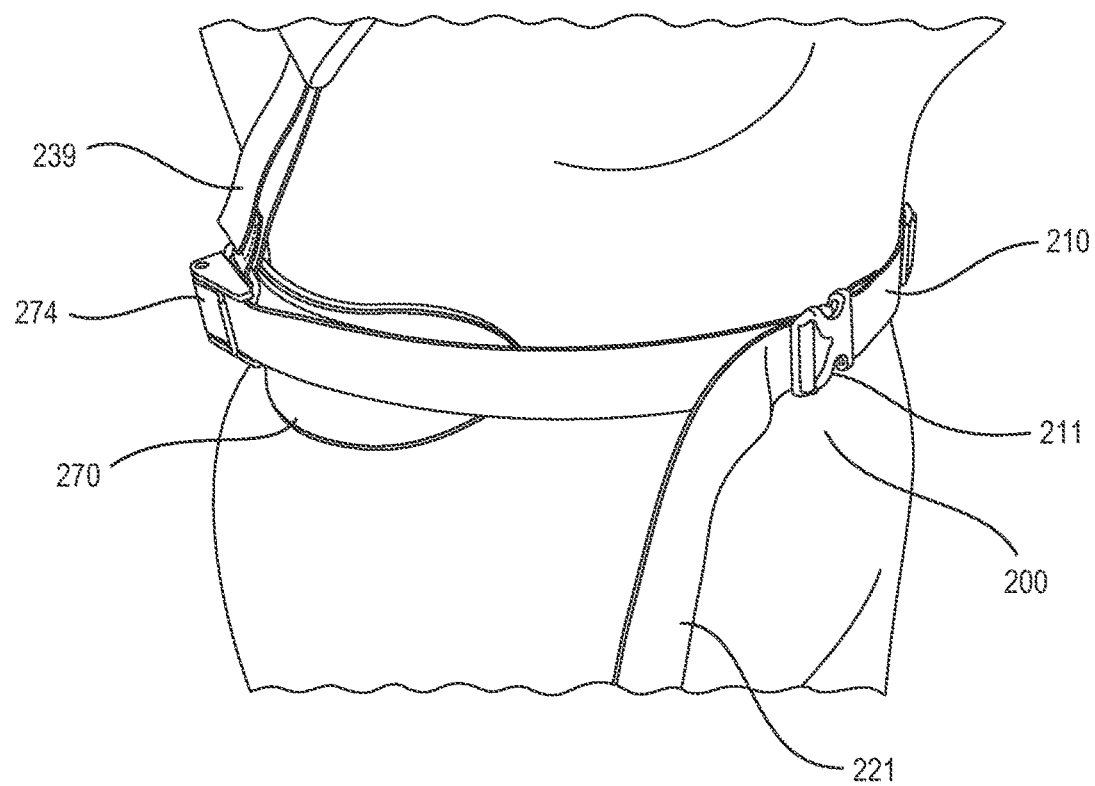
FIG. 2E is a close-up of the perspective anterior-lateral view of the exoskeleton interface system according to FIG. 2A.
Figure 2F:
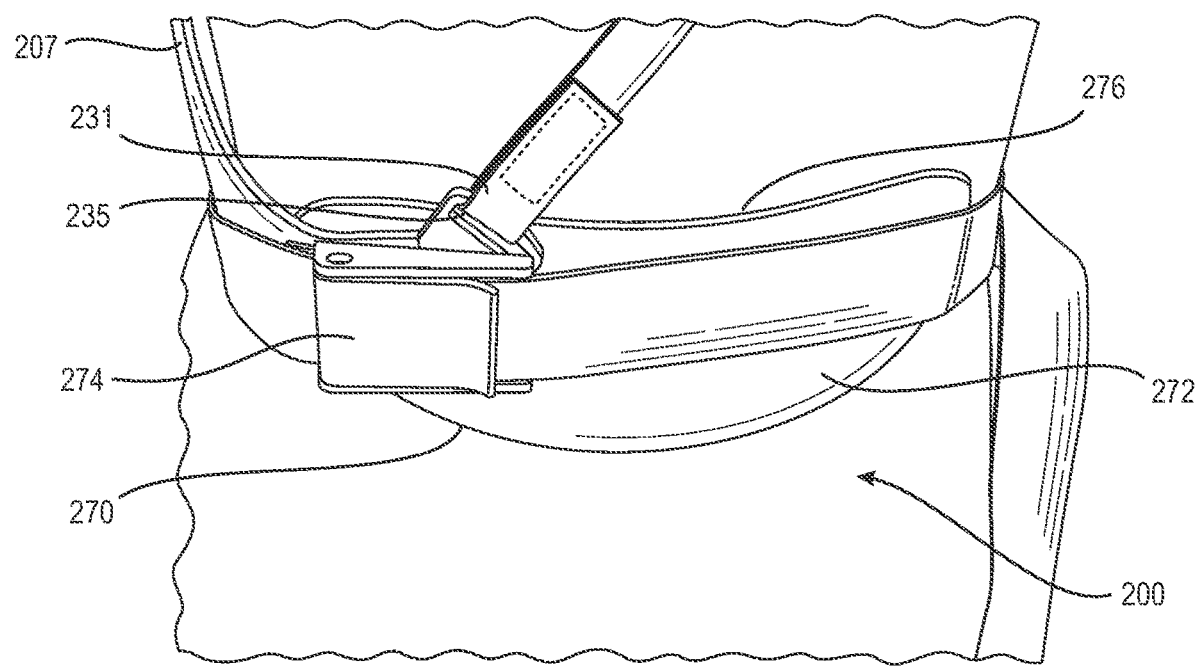
FIG. 2F is a close-up schematic lateral view of the exoskeleton interface system according to FIG. 2A.

Each right frame member and left frame member begins proximally at upper, laterally-extending transverse portions 262, 264 at a respective right and left scapulae, and extends downwardly and laterally through body portion 207 of the frame member, to the side of the torso where a distal end 260 of each right frame member and left frame member respectively attach to a support belt 210. FIG. 2D shows the distal end 260 of left frame member 212 attaches to support belt 210. A lateral torso pad 270, including an outer rigid material and a softer, inner material, is provided at each connection point of the left and right frame members to the support belt 210. These are designed to rest in the waist space between the inferior costal margin and over the wings of the ilium. The frame weight is thus transferred to the pelvis. Although lateral bending is somewhat compromised, the felt-weight (i.e., the weight perceived by the user) of the frame is reduced while flexion/extension motion of the lumbar spine remains effectively unencumbered. The shoulder-generated loads on the frame are transferred to the anterior anatomy at a greater distance from the shoulders, so the felt-weight and load and pressures on the skin of the user is reduced.

The interface of the embodiment of FIGS. 2A-2G further includes a strap assembly, including two shoulder straps 234 that extend over the shoulder of a user, and a connecting segment 231 that connects a lower, anterior portion of each of the shoulder straps 234 to a lower portion of the left and right frame member, respectively. Underlying shoulder strap pads 236 is provided at the shoulder segment of shoulder strap 234. Anterior chest strap 235 is provided connecting front portions of shoulder straps 234, with chest strap 235 being adjustable to accommodate various users' required chest dimensions. The chest buckle 233 is provided to unfasten the chest strap 235 to aid in donning and removing the interface 200. The length of connecting segment 231 can be adjusted by length adjustment fastener 237 to provide more or less excess strap length 239, appropriately and comfortably fit the shoulder strap 234 to the user, and adjust for the dimensions of the user's shoulder.

Figure 2G:
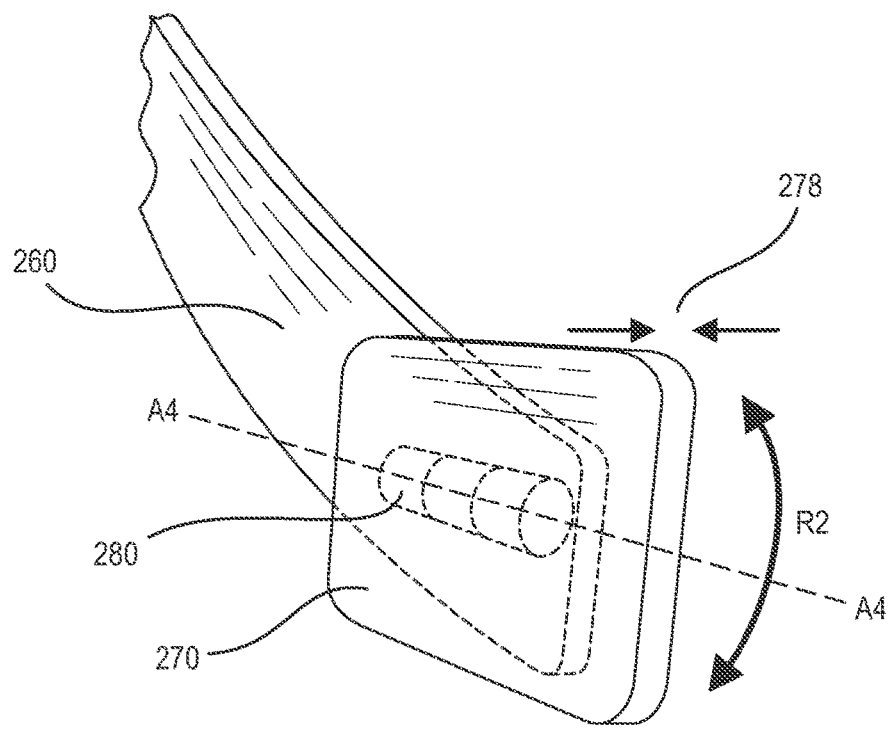
FIG. 2G shows a simple single-axis articulation that allows use of a sealed bearing.

In the embodiment of FIGS. 2A-2G, the interface frame, including first and second frame members 212, 214, wraps from scapula in the coronal plane down to the distal lateral end 260 of each frame member on the trunk in the sagittal plane. As shown in FIG. 2G, at the lower, distal lateral ends of each frame member, a torso pad 278 is provided, the contact point, having contact surface 270, on the user. The pad is attached to the frame via a hinge 280 oriented axially in the sagittal plane, with hinge 280 providing pivoting motion R2 around axis A4.

The hinged attachment allows the pad to pivot/articulate to accommodate the varying lateral contours of users. Although shown as having primarily plate members, the frame could be tubular for exceptional stiffness and reduced weight, while at its various attachment points, flattened regions could be created to facilitate articulations and stability between components. The frame could consist of injection molded components as well with appropriate flattened areas for articulation and stability. An injection-molded frame could facilitate simple integration of co-molded edges or surfaces to improve the user's comfort and reduce the likelihood of damaging other surfaces in the work environment.

The support belt 210 of the embodiment of FIGS. 2A-2G includes front buckle 211 provided for quick and convenient attachment and detachment upon donning and removing the interface. A lateral cam buckle 274 can be provided on both sides to ensure and customize the proper fit around the user's waist.

Figure 3C:
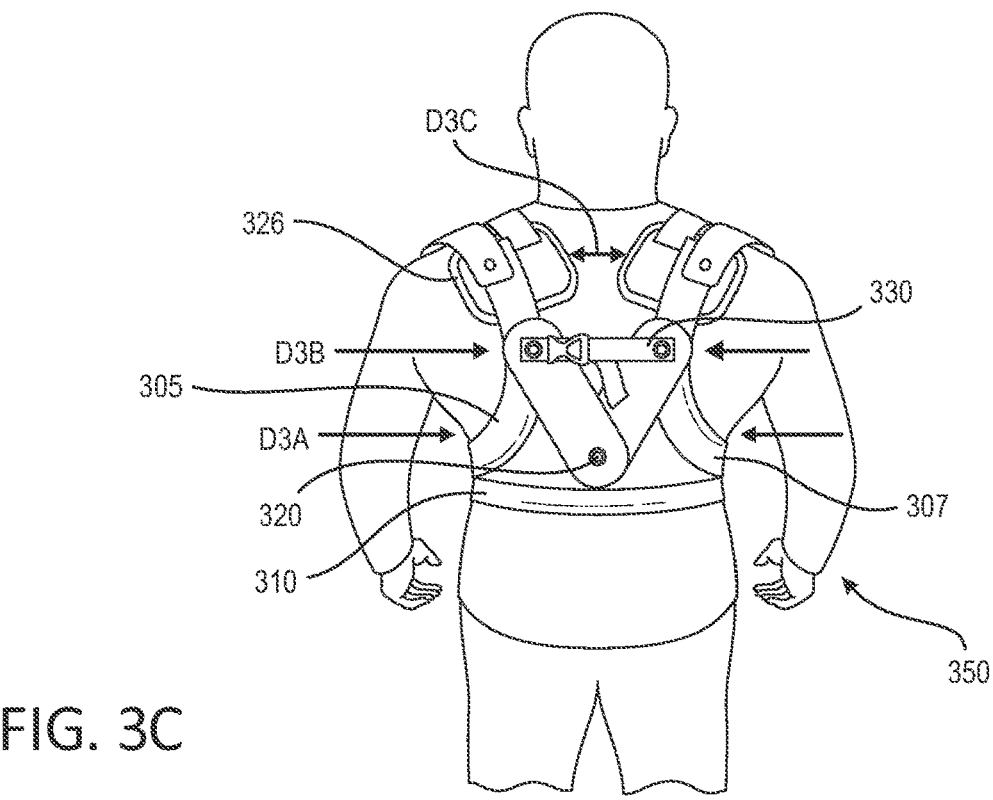
FIG. 3C shows a schematic posterior view of an embodiment of a short version of the exoskeleton interface system.

As shown in FIG. 3C, once donned, the lower belt affixes the distal aspects of the left and right frames to the lateral aspects of the user's respective left and right side of the user's trunk. An elastic strap or spring mechanism located on the hinge or between the frames facilitates the approximation of the upper aspect of the frames to the lateral aspects of the user's shoulders. The articulation facilitating proximal broadening-narrowing between frames in the coronal plane obviates the linear bearings (their respective maintenance, cost, and weight). The simple single-axis articulation will also allow a sealed bearing for a more waterproof or water-resistant design.

In another embodiment, an interface for an asymmetric, unilateral exoskeleton is provided, as shown in FIGS. 4A-4D. The inventor of the present invention has found and addressed the additional problem that not all activities require bimanual overhead tasks. Some work requires only a single-handed activity overhead such as painting. Considering potential medical conditions of works, a rotator cuff tear or shoulder impingement usually occurs only on one side. Thus, in such situations, there would be no need to utilize a bilateral exoskeleton. A unilateral exoskeleton such as this may help reduce the muscular effort of a single shoulder. The inventor's design described herein the above embodiments may be easily modified into a unilateral design. The right or left frame member being set up independently for unilateral use with a simple modification to the harness and belt.

Here again, to provide an interface for an asymmetric, unilateral exoskeleton, rather than a T-shaped monolithic strut centered on the spine and secured at the waist, with flexion actuators on the upper, horizontal members of the "T," the embodiment of FIGS. 4A-4D includes a frame 402 for an exoskeleton 400, the frame 402 having single left frame members 412, which independently attaches to respective left shoulder mount assemblies 440, to which a left actuator 404 may be mounted. Although a single left frame member is shown in this embodiment, another embodiment includes the mirror image of the embodiment of FIGS. 4A-4D, having a single right frame member instead.

The left frame member 412 extends downwardly from the point of attachment of the shoulder mount assembly 440 and is contoured around the lateral aspect of the torso of the user. According to this embodiment, the first (for example, left) frame member 412 extends downward, contouring laterally and connecting to the support belt 410. The left frame member begins proximally at upper, proximal portion 442 at a left scapula of the user, then transitions downward and laterally through body portion 407 of the frame member 412, to the side of the torso where a distal end 460 of the left frame member to attach to a support belt 410. This configuration reproduces the basic contact points for stabilization of the frame and delivers the assistive torque to the shoulder while it entirely minimizes the contact area/coverage of the body. As shown in FIG. 8, such an interface provides contact at the scapular fulcrum point (B) and counterforce (C), which is needed for the minimal interface stabilization scheme noted above while minimizing unnecessary contact against the user thereby increasing the efficiency of the dissipation of heat.

Figure 4A:
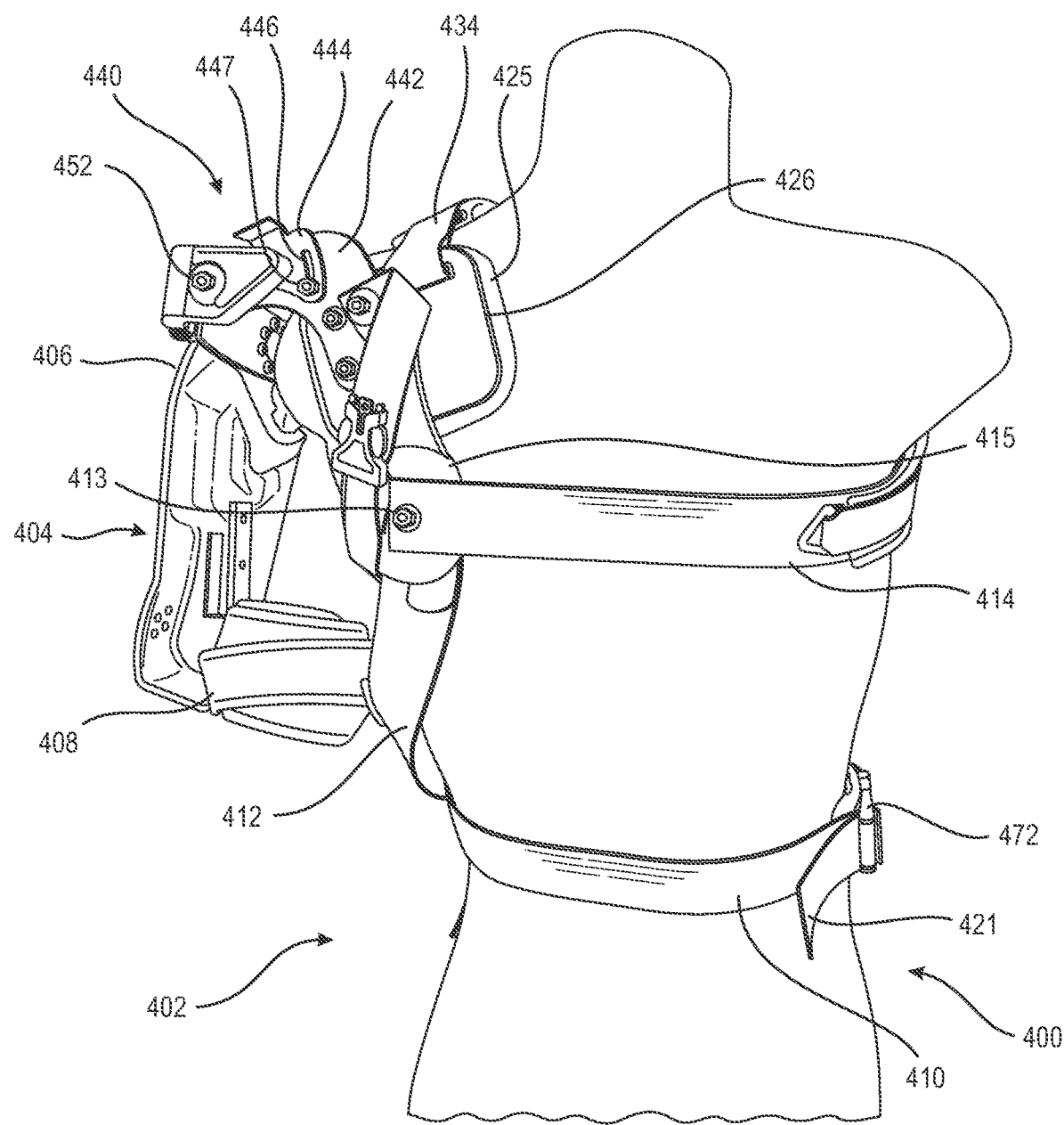
FIG. 4A is a schematic posterior view of another embodiment of an exoskeleton interface system.
Figure 4B:
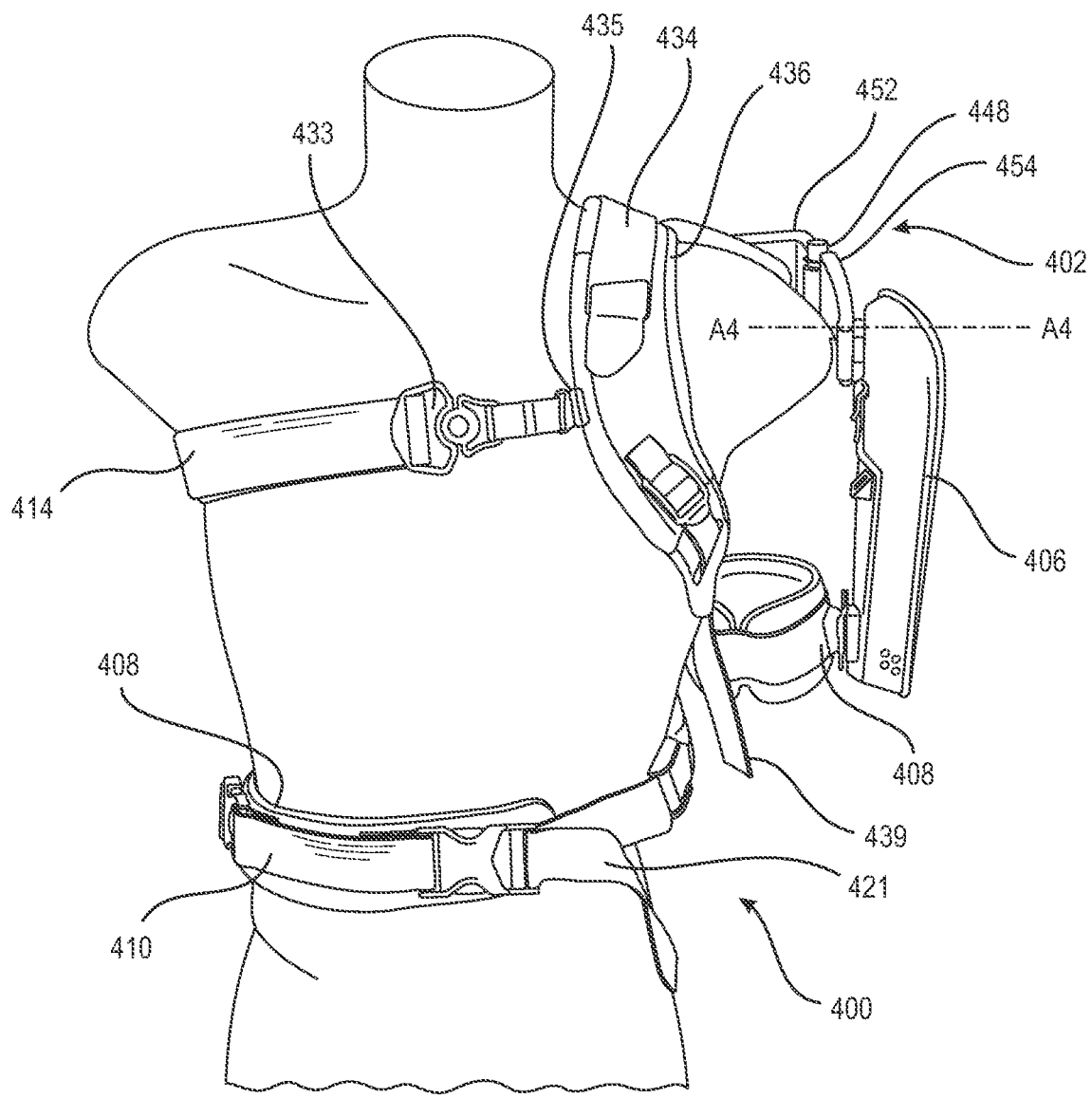
FIG. 4B is a schematic anterior view of the exoskeleton interface system according to FIG. 4A.
Figure 4C:
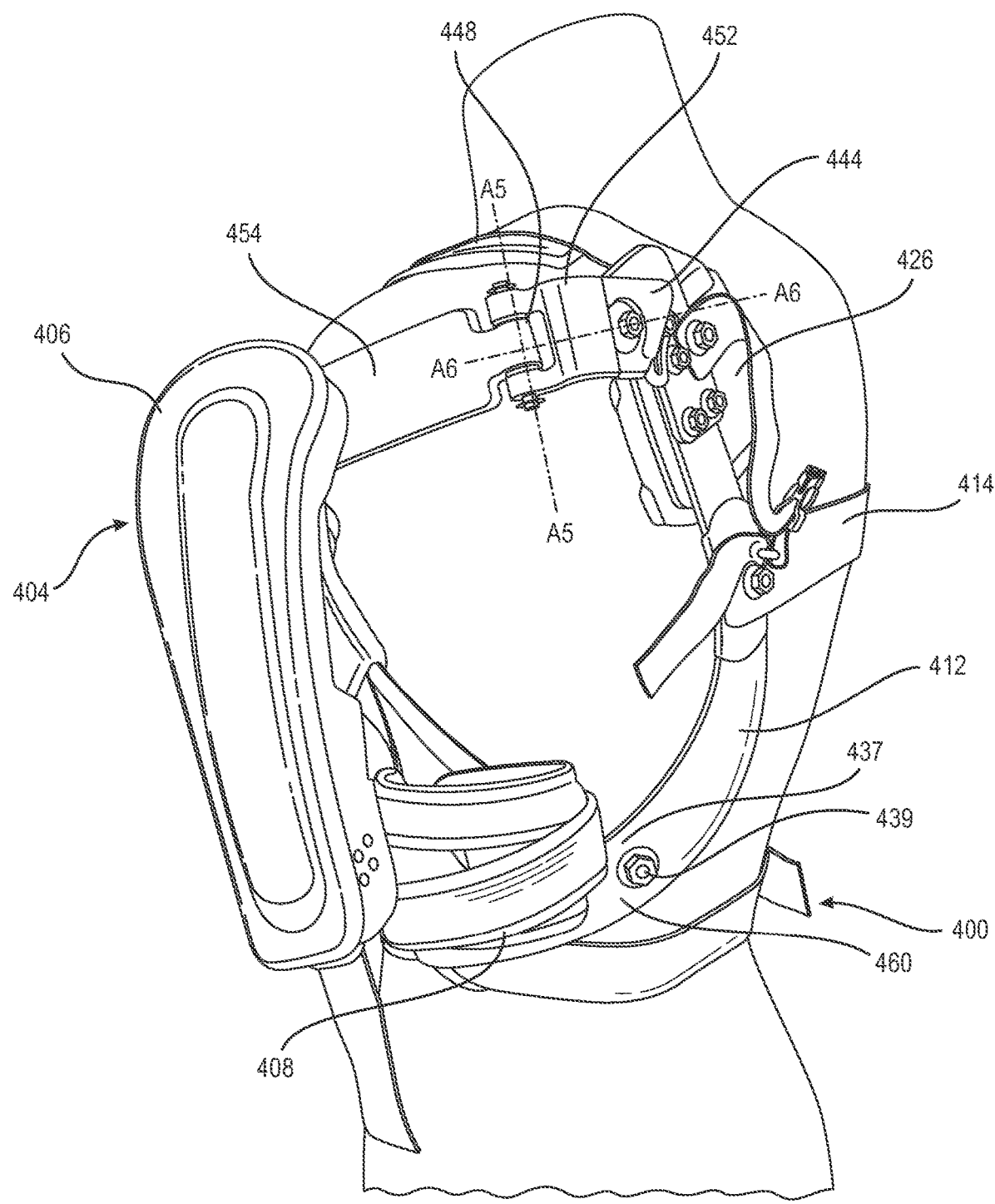
FIG. 4C is a schematic lateral view of the exoskeleton interface system according to FIG. 4A.

Once donned, the lower belt (support belt 410) affixes the distal (lower) end 460 of the left frame member to the lateral area of the user's respective left side at the user's trunk, as illustrated in FIGS. 4A, 4B, and 4C.

In the embodiment of FIGS. 4A-4D, the interface system further includes a strap assembly including a left shoulder strap 434 having a shoulder pad 436. Provided at the upper, proximal portion 442 of the left frame member, a rigid shoulder pad or scapular pad 426 is provided, preferably at the user's left scapula. Under each shoulder pad or scapular pad 426 a softer, supportive material 425 is provided for more comfortable contact with the user.

Also, at or near the upper, proximal portions 442 of the left frame member 412, shoulder mount assemblies 440 is provided that connect left actuator 404 to the upper, proximal portions of each of the left frame member 412. Shoulder mount assemblies 440 each include a respective shoulder support plate 444 with guide pin 447 and abduction track 446, and a shoulder abduction plate 454 attached to the shoulder support plate 444 by pivot connection 452.

Accordingly, up to three degrees of movement are provided with the embodiment of FIGS. 4A-4D. Horizontal shoulder abduction and adduction are permitted by vertically-oriented rotation hinge 448 oriented along direction A5. Humeral flexion and extension are permitted by a horizontally-oriented rotation hinge 450 oriented along direction A4. Additionally, actuator 404 provides humeral flexion assistance, with humeral cuff 408 which affixes to the user's humerus. Arm cuff 408 is adjustable to accommodate a considerable size range of users' arms and adjust relative to girth changes suitable for potential users and a user's arm changes during contraction. The third degree of movement is provided due to the pivoting around direction A6, as shown, for example, in FIG. 4C, in which a shoulder abduction plate 454 is pivotably attached to the shoulder support plate 444 by pivot connection 452. Alternatively, movement about the axis of A6 may be intentionally limited by preventing travel of guide pin or fastener 447 within guide track 446. As described in the embodiment of FIGS. 5 and 6A-6B, abduction assistance may also be provided through an additional actuator assembly.

Figure 4D:
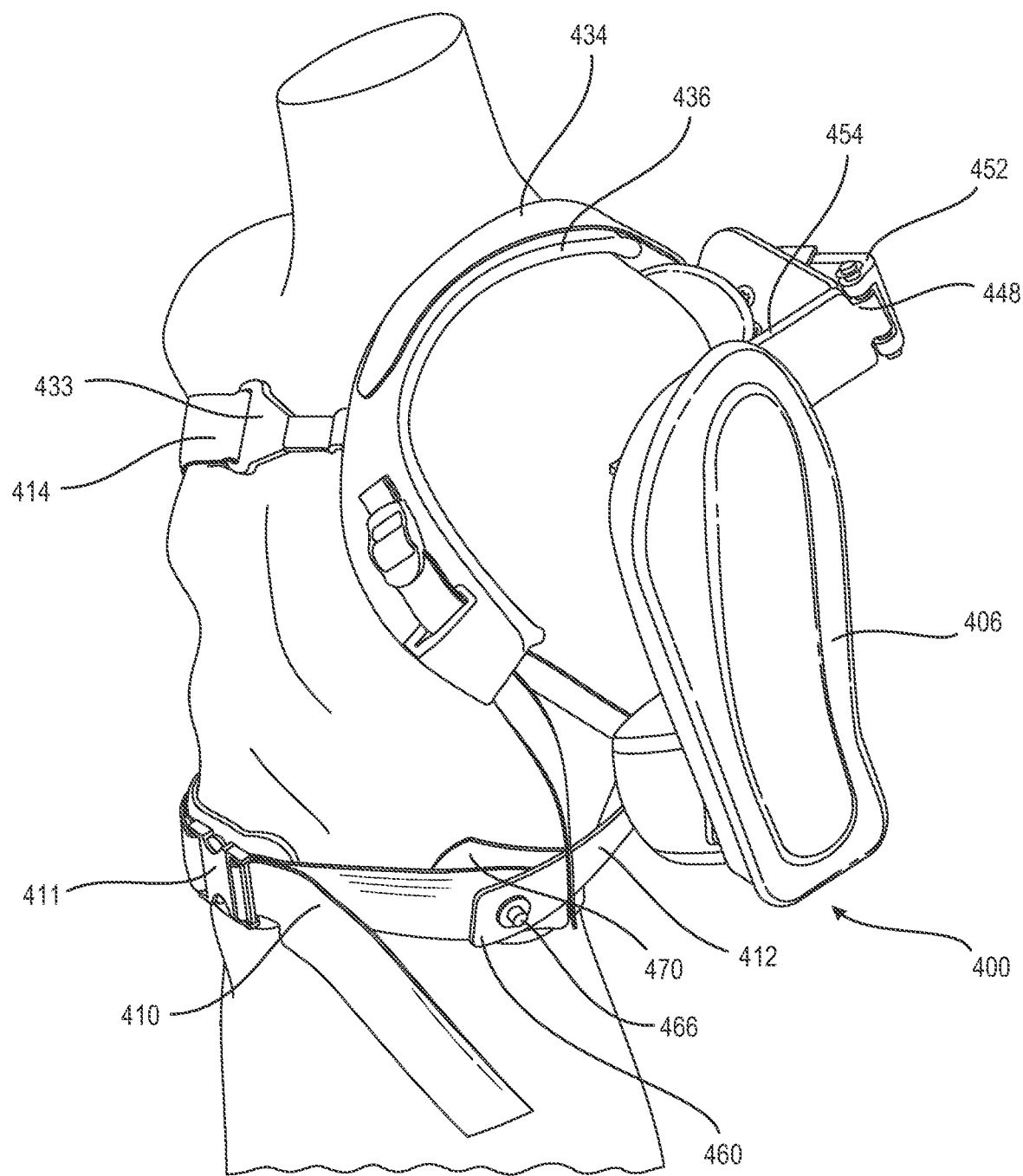
FIG. 4D is a schematic, perspective anterior-lateral view of the exoskeleton interface system according to FIG. 4A.

The left frame member begins proximally at upper, proximal portions 442 at the left scapula of the user, and extends downwardly and laterally through body portion 407 of the frame member 412, to the side of the torso where a distal end 460 attaches to a support belt 410. FIG. 4D shows the distal end 460 of left frame member 412 attaches to support belt 410 by fastener 466. A lateral torso pad 470, including an outer rigid material and a softer, inner material is provided at the connection point of the left frame member to the support belt 410.

The interface of the embodiment of FIGS. 4A-4D further includes a strap assembly, including a shoulder strap 434 that extends over the left shoulder of a user, and a connecting segment 431 that connects a lower, anterior portion of each of the shoulder strap 434 to a lower portion of the left frame member. Underlying shoulder strap pads 436 is provided at the shoulder segment of shoulder strap 434. Here the left shoulder strap is effectively converted into a figure-9 strap with the addition of a strap 414 that attaches to the formerly chest strap at the chest, but it now encircles around the trunk and attaches at the frame at the same approximate height with connector 413. The waist belt 410 is simply a continuous strap with the right half of the exoskeleton removed. The chest strap 414 is provided connecting front portions of shoulder straps 134, with chest strap 414 being adjustable to accommodate various users required chest dimensions. The chest buckle 433 is provided to unfasten the chest strap to aid in donning and removing the interface 400.

According to the embodiment shown in FIGS. 4A-4D, the same 3-point force system is employed to assist only the single left shoulder: (1) forward flexion force at mid humerus, (2) stabilizing fulcrum at the scapula, and (3) counterforce on strap being pulled posteriorly by the frame 400.

Figure 5:
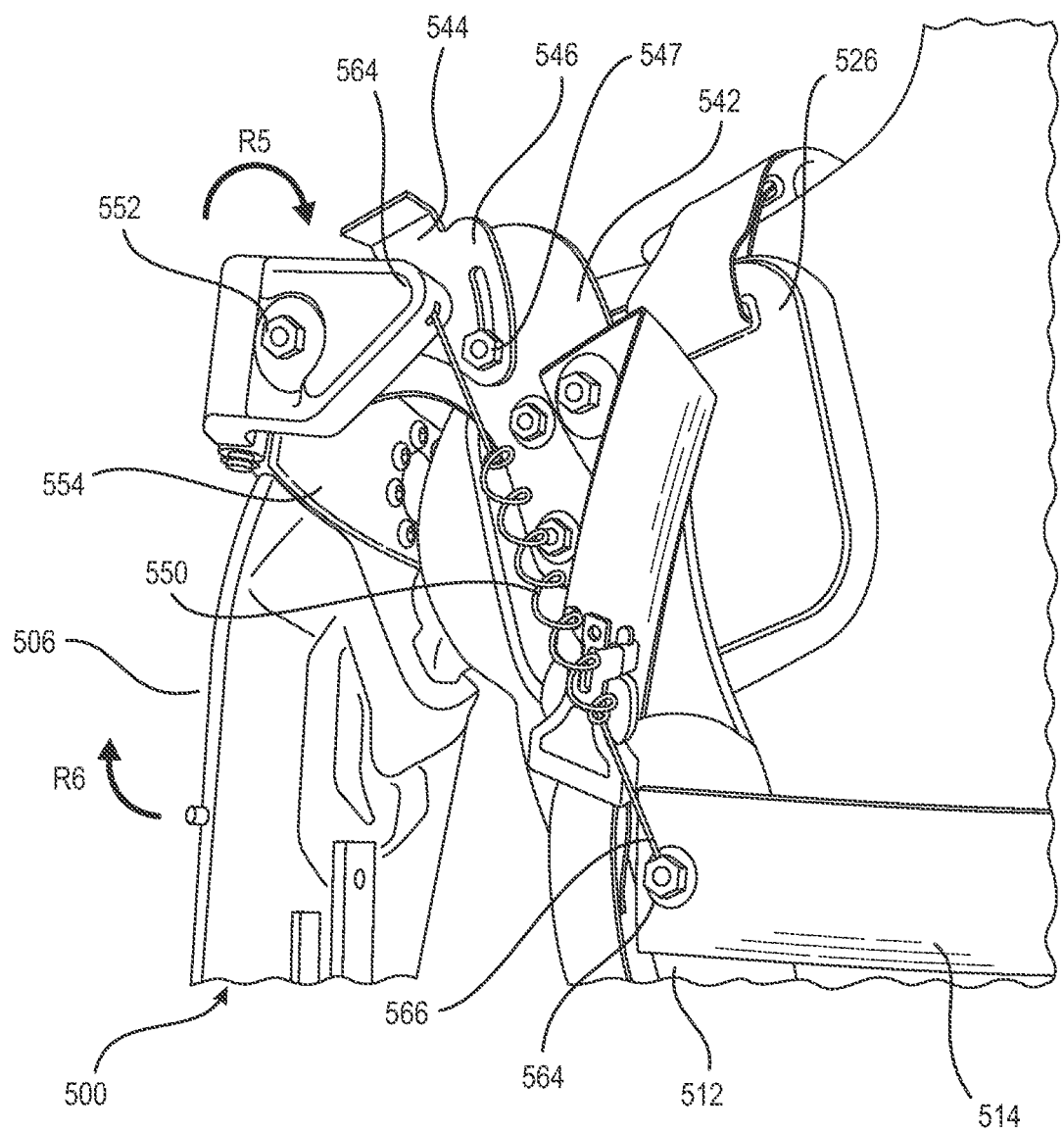
FIG. 5 shows a close-up view of a posterior view of another embodiment of the exoskeleton interface system.

Relating to the embodiment shown in FIG. 5, it is noted that abduction is, for the most part, a secondary motion for overhead work. The actuator and linkage illustrated in the above embodiments are designed to offer direct and measured assistance in humeral flexion specifically. Because of workers' possible medical conditions, the inventor has found that it would be helpful to offer specific abduction assistance as well, which is the key motion limited by the impingement or rotator cuff tear or repair due to the physical route of the musculature.

With the frame of the above-described embodiments having separate frame members, abduction assistance could easily be offered if a spring mechanism 550 or other force-applying mechanism is attached to the cantilevered hinge extension 464 already present on the abduction mechanism. The spring mechanism 550 is connected to frame member 512 at lower fastener 564. That is, at or near the upper, proximal portions 542 of the left frame member 512, shoulder mount assembly 540 is provided that connects left actuator 504, with an actuator box 506, to the upper, proximal portions of each of the left frame member 512. Shoulder mount assemblies 540 each include a respective shoulder support plate 544 with guide pin 547 and abduction track 546, and a shoulder abduction plate 554 attached to the shoulder support plate 544 by pivot connection 552. Such an arrangement would assist in the abduction movement of the shoulder of the user. Although this embodiment of shoulder abduction assistance is shown on the left shoulder of in the close-up image of FIG. 5, a mirror image of such an arrangement may also be included on the right frame member above the right shoulder.

The shoulder abduction assistance can be adjustable by replacing or tightening the spring. The spring mechanism 550 could include an adjustable tension clock spring, selectable constant force spring configuration, or incorporate an adjustable cam/spring mechanism in combination, which could adjust the amount of assistance offered in the abduction and or the angle at which peak torque assistance is offered.

Figure 6A:
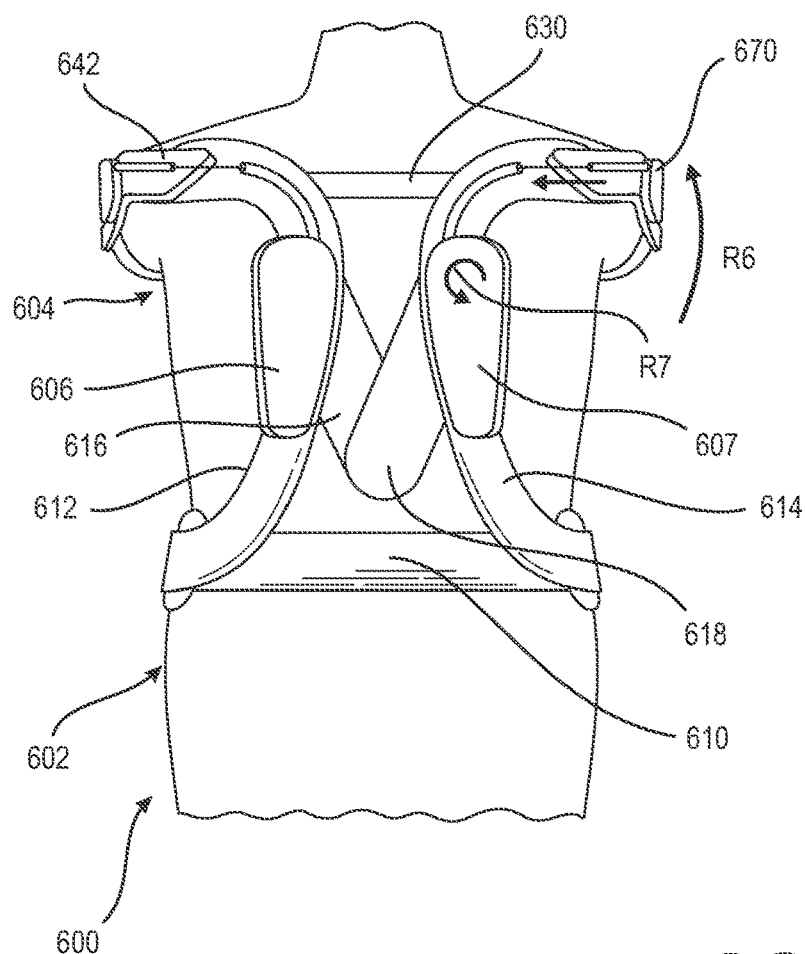
FIG. 6A shows a posterior view of another embodiment of the exoskeleton interface system.
Figure 6B:
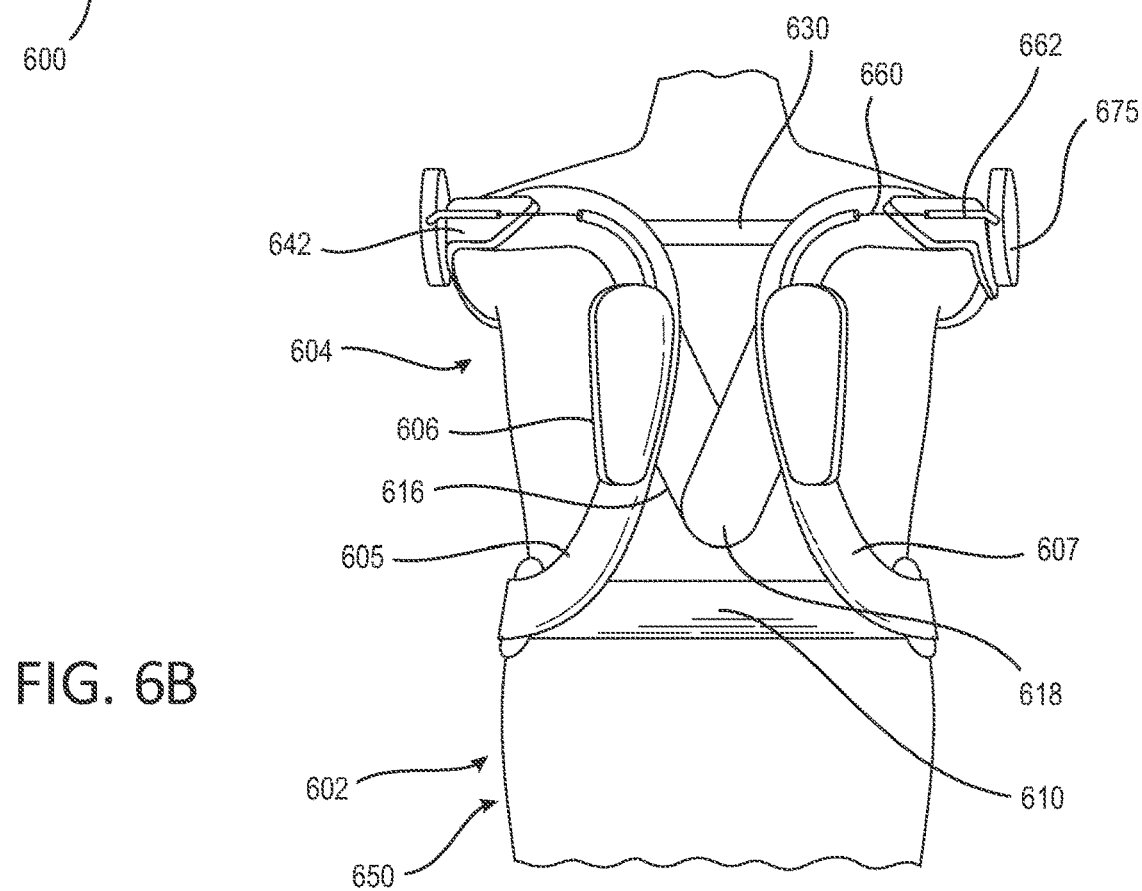
FIG. 6B shows a posterior view of another embodiment of the exoskeleton interface system.

A remote actuation system is provided in a further embodiment, which includes features that implementable in the above embodiments, as shown in FIGS. 6A and 6B. The interface 600 of this embodiment includes frame 602, with left and right frame members 612, 614, and left and right hinge plates 616, 618. A strap 630 connects upper portions of the left and right frame members and prevents lateral separation of the upper portions of the left frame member from the upper portion of the right frame member beyond a predetermined distance in the coronal plane. Left and right actuator assemblies 606, 607 are provided attached to the respective left and right frame members 612, 614. The actuators can be moved away from the shoulders and attached centrally on the trunk. A Bowden cable system including an actuator cable 660 within a housing 662, such as that used in bicycle brakes, can be routed to the shoulders to provide a torque to rotating mechanisms attached at the shoulders and drive the flexion actuation remotely. Such remote actuators may also provide shoulder abduction actuation remotely. The actuators pull on actuator cable 660 cables that are routed to the shoulder.

The shoulder flexion actuation could be driven by any (or the same) actuation devices but the assistive torque would be delivered by cable remotely to the shoulders. The cables route into a rotating attachment on the lateral aspects of the shoulders. Rather than the actuators rotating a bar attached to a cuff on the arm, as shown in the above embodiments, the actuators pull with a similar force on a cable routed to a fixed spool attached to and creating torque on a rotating bar with the cuff on the arm. As shown in FIG. 6B are large disc attachments. FIG. 6A shows an embodiment with a minimally sized attachment mechanism. This attachment mechanism would preferably be small diameter and of a low profile given the required minimum cable bends and variable torque assistance at the shoulder.

By providing an interface system for an exoskeleton system as described herein, the problems of related exoskeleton devices which do not efficiently dissipate heat from the user, are perceived by the user to limit movement, and do not provide necessary assistive forces, are overcome by the provision of an improved interface system with a support belt, a strap assembly, and at least one or two separate frame member as described herein.

It should be understood that not necessarily all objects or advantages may be achieved under any embodiment of the disclosure. The embodiments may be embodied or carried out to achieve or optimize one advantage or group of advantages as taught without achieving other objects or advantages as taught or suggested.

The various features described herein should be understood to be interchangeable. Besides the variations described, other known equivalents for each feature can be mixed and matched by ordinary skill in this art to construct an interface system under principles of the present disclosure.

While the shoulder assist mechanism is briefly described, it is not limited to the depicted embodiments and the interface system may be adapted to accommodate different shoulder assist mechanisms.

The invention claimed is:

1. An interface system for an exoskeleton, the interface system comprising:
   a support belt;
   a strap assembly including respective first and second shoulder straps adapted to extend around a user's shoulders, each of the first and second shoulder straps being adjustable in length; and
   a frame system that includes a first frame member,
   the first frame member having an upper attachment portion configured to have a first assistive device attached thereto at a shoulder mount assembly,
   the first frame member connected to the first shoulder strap of the strap assembly and extending from a user's left or right scapula downward contouring laterally and connecting to the support belt, the first shoulder strap connecting to proximal and distal ends of the first frame member;

wherein the frame system includes a second frame member connected to the second shoulder strap of the strap assembly and extending downward contouring laterally and connecting to the support belt, the second shoulder strap connecting to proximal and distal ends of the second frame member;

wherein the first frame member and the second frame member are shaped to contour laterally in opposed directions;

the first frame member connected posteriorly to the second frame member through a pair of hinge arms joined at a pivot connection.

2. The interface system according to claim 1, wherein the first frame member is connected posteriorly to the second frame member through a pair of hinge arms joined at a pivot connection.

3. The interface system of claim 2, having an upper attachment portion configured to have a second assistive device attached thereto at a second shoulder mount assembly.

4. The interface system according to claim 2, wherein the support belt includes belt segments configured to connect on an anterior side of a user.

5. The interface system according to claim 2, wherein the first frame member and the second frame member each have a respective length to extend to the support belt arranged at a user's lower thoracic vertebrae.

6. The interface system according to claim 2, wherein the first frame member and the second frame member each have a respective length to extend to the support belt arranged at a user's iliac crest.

7. The interface system according to claim 2, wherein the shoulder mount assembly of the first frame member includes a first scapular pad arranged at a user's left or right scapula, and the first frame member extends from the first scapular pad in a downward direction contouring laterally and connecting to a contact portion of the support belt without contact of the first frame member and the user between the first scapular pad and the contact portion of support belt.

8. The interface system according to claim 2, wherein the pivot connection is a hinge and the first frame member and second frame member each extend downward contouring laterally and connecting to the support belt in a generally symmetric manner with respect to a sagittal plane of a user.

9. The interface system according to claim 2, where the support belt includes a first hip pad at the connection of the first frame member to the support belt and a second hip pad the connection of the second frame member to the support belt.

10. The interface system according to claim 2, further comprising an adjustable strap, elastic mechanism, or spring mechanism connecting an upper portion of the first frame member to an upper portion of the second frame member such that the adjustable strap, elastic mechanism, or spring mechanism prevents lateral separation of the upper portion of the first frame member from the upper portion of the second frame member beyond a predetermined distance.

11. An interface system for an exoskeleton, the interface system comprising:
a support belt;
a strap assembly; and
a frame system that includes a first frame member and a second frame member,
the first frame member having an upper attachment portion configured to have a first assistive device attached thereto at a first shoulder mount assembly,
the second frame member having an upper attachment portion configured to have a second assistive device attached thereto at a second shoulder mount assembly,
the first frame member connected to the strap assembly and extending downward contouring laterally and connecting to the support belt,
the second frame member connected to the strap assembly and extending downward contouring laterally and connecting to the support belt,
the first frame member and the second frame member contouring laterally in opposed directions, and
the first frame member connected posteriorly to the second frame member through a pair of hinge arms joined at a pivot connection.

12. An exoskeleton assistive system comprising:
an interface system; and
a first assistive device attached to the interface system; and
a second assistive device attached to the interface system,
where the interface system includes
a support belt;
a strap assembly; and
a frame system that includes a first frame member and a second frame member,
the first frame member having an upper attachment portion to which the first assistive device is connected at a shoulder mount assembly,
the second frame member having an upper attachment portion to which the second assistive device is connected at a shoulder mount assembly,
the first frame member connected to the strap assembly and extending downward contouring laterally and connecting to the support belt,
the second frame member connected to the strap assembly and extending downward contouring laterally and connecting to the support belt,
the first frame member and the second frame member contouring laterally in opposed directions, and
the first frame member connected posteriorly to the second frame member through a pair of hinge arms joined at a pivot connection;
wherein the first frame member and the second frame member each have a respective length to extend to the support belt arranged at a user's lower thoracic vertebrae;
wherein the first frame member and the second frame member each have a respective length to extend to the support belt arranged at a user's iliac crest;
wherein the shoulder mount assembly of the first frame member includes a first scapular pad arranged at a user's left or right scapula, and the first frame member extends from the first scapular pad downward contouring laterally and connecting to a contact portion of the support belt without contact of the first frame member and the user between the first scapular pad and the contact portion of support belt;
wherein the pivot connection is a hinge and the first frame member and second frame member each extend downward contouring laterally and connecting to the support belt in a generally symmetric manner with respect to a sagittal plane of the user.

13. The interface system according to claim 11, wherein the support belt includes belt segments configured to connect on an anterior side of a user.

14. The interface system according to claim 11, wherein the first frame member and the second frame member each have a respective length to extend to the support belt arranged at a user's lower thoracic vertebrae.

15. The interface system according to claim 11, wherein the first frame member and the second frame member each have a respective length to extend to the support belt arranged at a user's iliac crest.

16. The interface system according to claim 11, wherein the shoulder mount assembly of the first frame member includes a first scapular pad arranged at a user's left or right scapula, and the first frame member extends from the first scapular pad extending in a downward direction contouring laterally and connecting to a contact portion of the support belt without contact of the first frame member and the user between the first scapular pad and the contact portion of support belt.

17. The interface system according to claim 11, wherein the pivot connection is a hinge and the first frame member and second frame member each extend downward contouring laterally and connecting to the support belt in a generally symmetric manner with respect to a sagittal plane of a user.

18. The interface system according to claim 11, a strap assembly includes a first shoulder strap adapted to extend around a user's shoulder, the first shoulder strap being adjustable in length;

wherein the first shoulder strap connects to proximal and distal ends of the first frame member.

19. The interface system according to claim 11, a strap assembly includes a second shoulder strap adapted to extend around a user's shoulder, the second shoulder strap being adjustable in length;

wherein the second shoulder strap connects to proximal and distal ends of the second frame member.

\* \* \* \* \*